US011819337B2

United States Patent
Savage

(10) Patent No.: US 11,819,337 B2
(45) Date of Patent: Nov. 21, 2023

(54) INGESTIBLE ELECTRONIC MEDICAL DEVICE

(71) Applicant: OTSUKA PHARMACEUTICAL CO., LTD., Tokyo (JP)

(72) Inventor: George M. Savage, Redwood City, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 887 days.

(21) Appl. No.: 16/632,209

(22) PCT Filed: Jul. 20, 2018

(86) PCT No.: PCT/US2018/043082
§ 371 (c)(1),
(2) Date: Jan. 17, 2020

(87) PCT Pub. No.: WO2019/018762
PCT Pub. Date: Jan. 24, 2019

(65) Prior Publication Data
US 2020/0229758 A1    Jul. 23, 2020

Related U.S. Application Data

(60) Provisional application No. 62/534,850, filed on Jul. 20, 2017.

(51) Int. Cl.
*G16H 20/10* (2018.01)
*A61B 5/00* (2006.01)
(Continued)

(52) U.S. Cl.
CPC ............ *A61B 5/4833* (2013.01); *A61B 5/073* (2013.01); *A61B 5/1473* (2013.01);
(Continued)

(58) Field of Classification Search
CPC .................................. G16H 20/13; A61J 7/02
(Continued)

(56) References Cited

U.S. PATENT DOCUMENTS

2002/0132226 A1    9/2002    Nair et al.
2003/0191430 A1    10/2003   D'Andrea et al.
(Continued)

FOREIGN PATENT DOCUMENTS

| JP | 2010-524512 | 7/2010 |
| JP | 2011-527802 | 11/2011 |

(Continued)

OTHER PUBLICATIONS

International Search Report and Written Opinion for International PCT Application No. PCT/US2018/043082, dated Nov. 7, 2018.
(Continued)

*Primary Examiner* — Timothy R Waggoner
(74) *Attorney, Agent, or Firm* — Pillsbury Winthrop Shaw Pittman, LLP

(57) ABSTRACT

A system to track consumer patient adherence to a drug and dose form includes a tracking device, a computer system and a database. The tracking device, to process a plurality of Ingestible Event Marker (IEM) devices, wherein each IEM device includes an IEM storing an IEM identifier code, may include a first capacitive plate, a second capacitive plate, and a structure to position each IEM device in proximity to the first and second capacitive plates. The tracking device may be configured to interrogate each IEM, via capacitive coupling, as each IEM device passes through the structure. The computer system communicatively coupled to the tracking device may be configured to receive each IEM identifier code read from each interrogated IEM and the database to track each IEM may be configured to link each received IEM
(Continued)

identifier code to additional information including an identifier of an active drug/medication.

14 Claims, 19 Drawing Sheets

(51) Int. Cl.
    *A61B 5/07*         (2006.01)
    *A61B 5/145*       (2006.01)
    *A61B 5/1473*     (2006.01)
    *A61J 3/07*         (2006.01)

(52) U.S. Cl.
    CPC ........ *A61B 5/14546* (2013.01); *A61B 5/6861* (2013.01); *A61J 3/07* (2013.01); *G16H 20/10* (2018.01); *A61J 2200/30* (2013.01); *A61J 2205/60* (2013.01)

(58) Field of Classification Search
    USPC ........................................................ 414/675
    See application file for complete search history.

(56) References Cited

U.S. PATENT DOCUMENTS

| | | | | |
|---|---|---|---|---|
| 2008/0284599 | A1* | 11/2008 | Zdeblick | ................ A61B 5/073 340/572.1 |
| 2009/0256702 | A1* | 10/2009 | Robertson | ............ A61B 5/4833 361/728 |
| 2010/0185055 | A1 | 7/2010 | Robertson et al. | |
| 2011/0009715 | A1 | 1/2011 | O'Reilly et al. | |
| 2012/0024889 | A1* | 2/2012 | Robertson | ............... A61J 3/007 222/23 |
| 2013/0328416 | A1* | 12/2013 | Whitworth | ................ F03G 5/06 307/149 |
| 2016/0380708 | A1* | 12/2016 | Dua | ...................... H04W 52/18 375/219 |
| 2017/0095405 | A1* | 4/2017 | Afsarifard | ............. A61J 7/0472 |
| 2017/0290513 | A1 | 4/2017 | O'Reilly et al. | |
| 2018/0125760 | A1* | 5/2018 | Chessa | .................. G01G 19/00 |

FOREIGN PATENT DOCUMENTS

| | | |
|---|---|---|
| JP | 2014-507922 | 7/2012 |
| KR | 10-2011-0039236 A | 4/2011 |
| KR | 10-2012-0012130 A | 2/2012 |
| KR | 10-2013-0135292 A | 12/2013 |
| WO | 2010/005877 A2 | 1/2010 |
| WO | 2012/092209 A2 | 7/2012 |
| WO | 2019018762 A1 | 1/2019 |

OTHER PUBLICATIONS

Office Action and Search Report with English translation dated Dec. 1, 2021, issued in the corresponding Taiwanese Patent Application No. 107124936.0, pp. 1-25.

Office Action dated Sep. 22, 2022, issued in the corresponding Japanese Patent Application No. 2020-052387, pp. 1-2.

Office Action issued in corresponding Korean Patent Application No. 10-2020-7004171, dated Feb. 10, 2023.

* cited by examiner

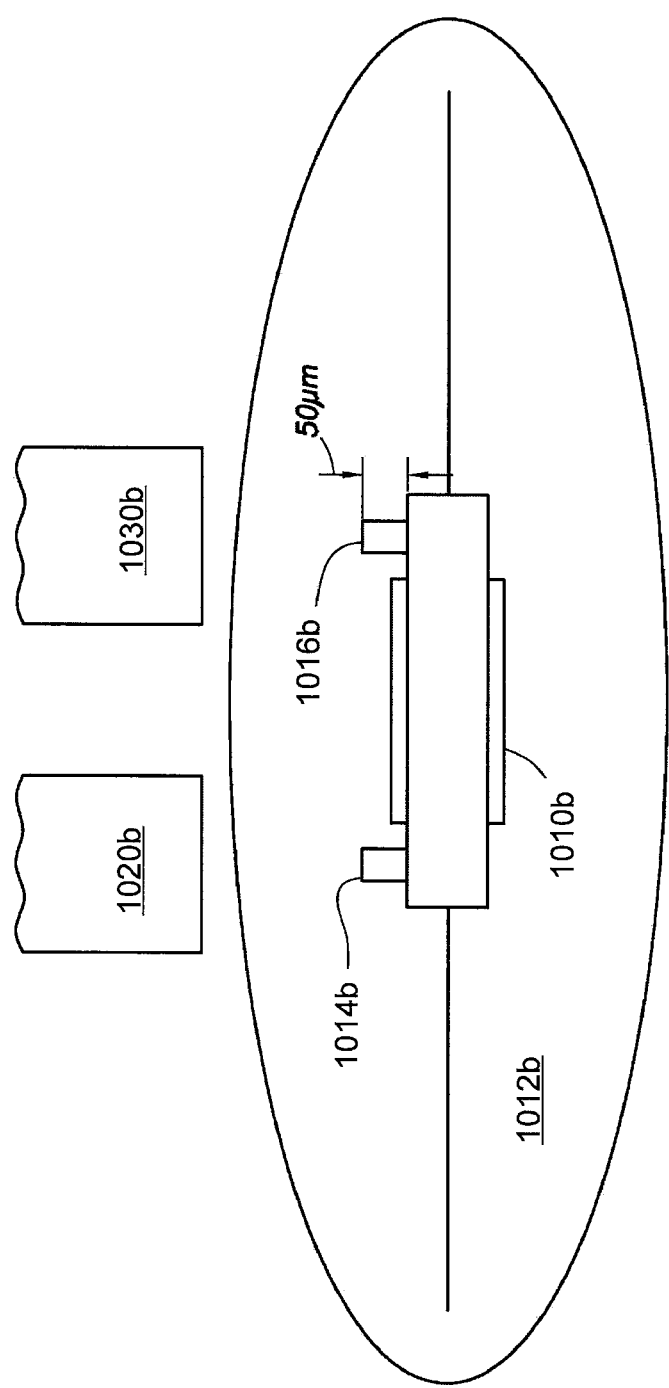

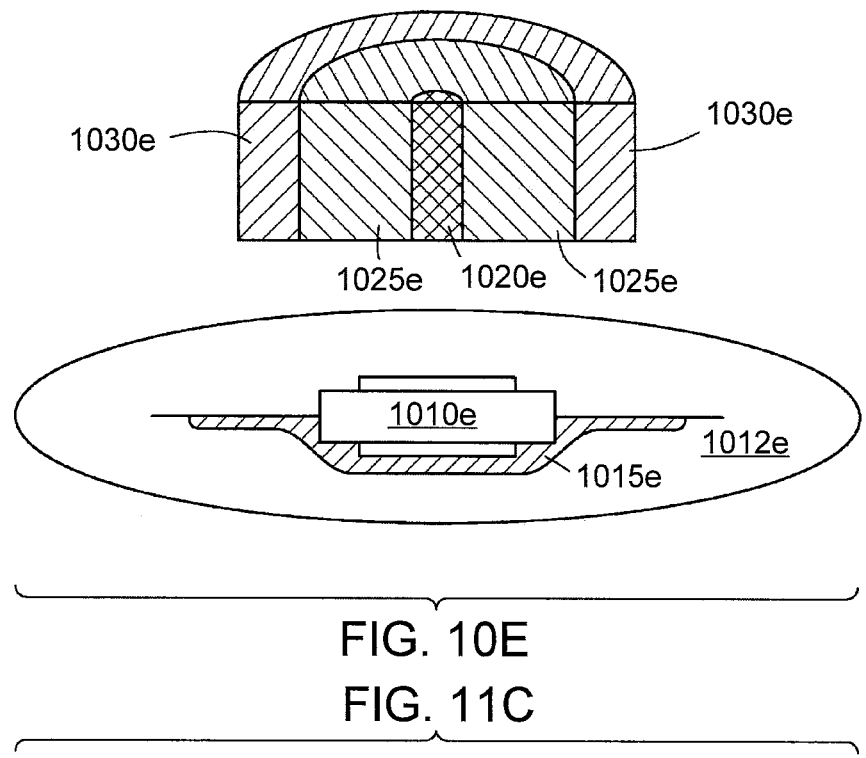
FIG. 10E
FIG. 11C
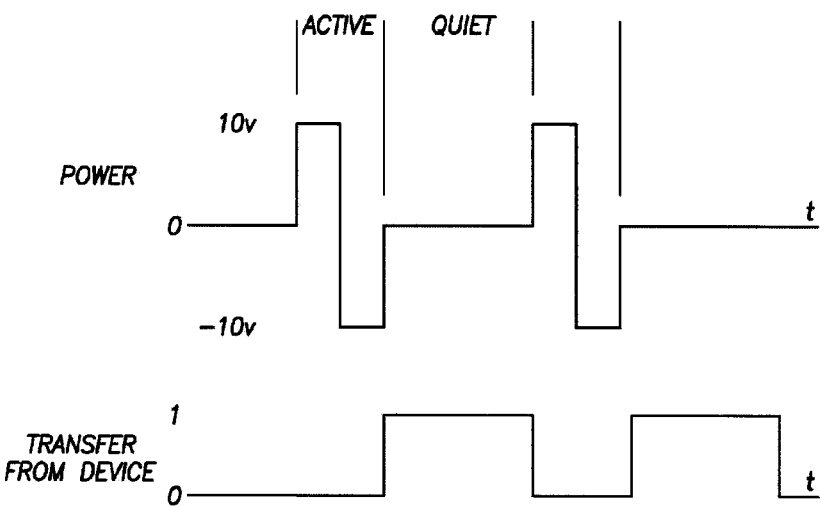

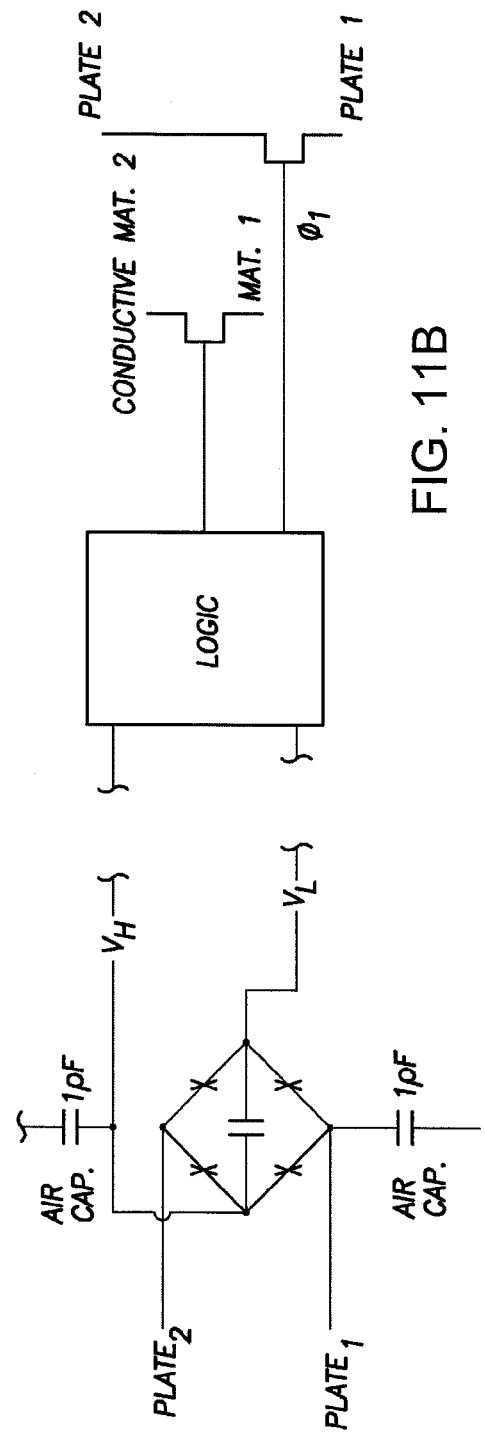

INGESTIBLE ELECTRONIC MEDICAL DEVICE

CROSS-REFERENCE TO RELATED APPLICATIONS

This application is a U.S. national stage filing under 35 U.S.C. § 371 of International Application No. PCT/US2018/043082, filed Jul. 20, 2018, entitled INGESTIBLE ELECTRONIC MEDICAL DEVICE, which claims the benefit of U.S. Provisional Application No. 62/534,850, filed Jul. 20, 2017, each of which is hereby incorporated by reference in their entirety.

BACKGROUND

Healthcare concerns related to pharmaceutical products include consumer patient error, misuse of medication, and lack of medication adherence. The present disclosure is related to methods, devices and systems to track pharmaceutical products from a manufacturer to a consumer patient and to monitor medication adherence.

SUMMARY

Proteus Digital Health, Inc. manufactures an Ingestible Event Marker (IEM) that is programmed with an identification code (IEM identifier code). This IEM may be incorporated into a placebo tablet. This form-factor is called an MIT (IEM-In-Tablet). In one aspect, an IEM can be integrated directly into a drug tablet/pill or a drug-containing capsule at the factory, at which point the dose form becomes a drug-device combination product subject to additional FDA approval prior to marketing. In another aspect, an IEM may be co-encapsulated (CoE) with one or more drugs/medications by a licensed pharmacist as directed by a physician prescription.

When wetted in the stomach, an IEM activates and conveys its unique identification code conductively through body tissues to a compatible receiver (e.g., a Band Aid-like adhesive Wearable Sensor (WS)). The WS logs detected IEM (e.g., and their respective identification codes) and may also track various physiological parameters (e.g., heart rate, activity, etc.). Data is periodically uploaded from the WS to a primary display of an external device (e.g., a smartphone or a tablet computer). Once on the external device, the data may optionally be relayed to a cloud-based personal health record, other local applications, or other data stores, depending upon the use case.

The FDA-cleared Indications for Use for the Proteus Digital Health Feedback Device (PDHFD), which includes the IEM, states in part: "When co-ingested with medication, the tracking and trending of intake times may be used as an aid to measure medication adherence." (c.f., K150494).

Proteus IEMs can be interrogated non-destructively after incorporation into placebo tablets, drug tablets/pills, or drug-containing capsules. In one aspect, a Wireless Interrogator (WI) operates in the kV range by capacitive-coupling an AC (50 kHz) signal to an IEM. This external signal powers the IEM, which then switches its internal antenna in and out of the circuit, modulating the capacitance sensed by the WI and thereby conveying information. In such an aspect, the unique identification code (e.g., IEM identifier code) and configuration of each IEM can be read out at the time of manufacture or subsequently.

An IEM associated with a pharmaceutical product may be used to confirm consumption of the proper drug and dose form by a consumer patient. The present disclosure is related to the technical challenges associated with the mapping of digi-codes (individually programmed IEM identifier codes) to specific ingestion events (e.g., of a drug and dose form, such as Furosemide, 20 mg tablet) to monitor consumer patient adherence to a prescribed pharmaceutical therapeutic regimen.

In one aspect of the present disclosure, a system to track consumer patient adherence to a drug and dose form including a tracking device, a computer system and a database is provided. The tracking device, to process a plurality of Ingestible Event Marker (IEM) devices, wherein each IEM device includes a stored IEM identifier code, may include a first capacitive plate, a second capacitive plate, and a structure to position each IEM device in proximity to the first and second capacitive plates. The tracking device may be configured to interrogate each IEM, via capacitive coupling, as each IEM device passes through the structure. The computer system communicatively coupled to the tracking device may be configured to receive each IEM identifier code read from each interrogated IEM and the database to track each IEM may be configured to link each received IEM identifier code to additional information including an identifier of an active drug/medication.

In another aspect of the present disclosure a system to track consumer patient adherence to a drug and dose form including a computer system including a compliance application to identify at least one active drug and dose form associated with at least one Ingestible Event Marker (IEM) identifier code is provided. The compliance application may be configured to: i) receive an IEM identifier code associated with an ingested IEM, ii) detect whether the received IEM identifier code is an unknown IEM identifier code, iii) query an IEM tracking system database using the unknown IEM identifier code to identify an active drug and dose form associated with the ingested IEM, wherein the IEM tracking system database stores IEM data including a plurality of active drug and dose forms mapped to a plurality of IEM identifier codes post-production of the IEMs, and iv) receive the active drug and dose form mapped to the unknown IEM identifier code from the IEM tracking system database to confirm consumer patient adherence associated with the active drug and dose form.

In yet another aspect of the present disclosure, a system to track consumer patient adherence to a drug and dose form including a pharmacy system including a tracking device, a computer system, a database and a transmission unit is provided. The tracking device, to process a plurality of Ingestible Event Marker (IEM) devices, wherein each IEM device includes an IEM storing an IEM identifier code, and wherein each IEM is stably associated with a non-drug composition co-encapsulated with an active drug, may include a first capacitive plate, a second capacitive plate, and a structure to position each IEM device in proximity to the first and second capacitive plates. The tracking device may be configured to interrogate each IEM, via capacitive coupling, as each IEM device passes through the structure. The computer system communicatively coupled to the tracking device may configured to receive each IEM identifier code read from each interrogated IEM, the database to track each IEM may be configured to link each received IEM identifier code to an identifier of the active drug, and the transmission unit may be configured to transmit each received IEM identifier code and the identifier of the active drug linked to each received IEM identifier code to an IEM tracking system database for use in tracking consumer patient adherence to at least one active drug and dose form.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

Further, it is understood that any one or more of the following-described forms, expressions of forms, examples, can be combined with any one or more of the other following-described forms, expressions of forms, and examples.

The foregoing summary is illustrative only and is not intended to be in any way limiting. In addition to the illustrative aspects, and features described above, further aspects, and features will become apparent by reference to the drawings and the following detailed description.

FIGURES

The novel features of the various aspects described herein are set forth with particularity in the appended claims. The various aspects, however, both as to organization and methods of operation may be better understood by reference to the following description, taken in conjunction with the accompanying drawings as follows:

Figure 9:
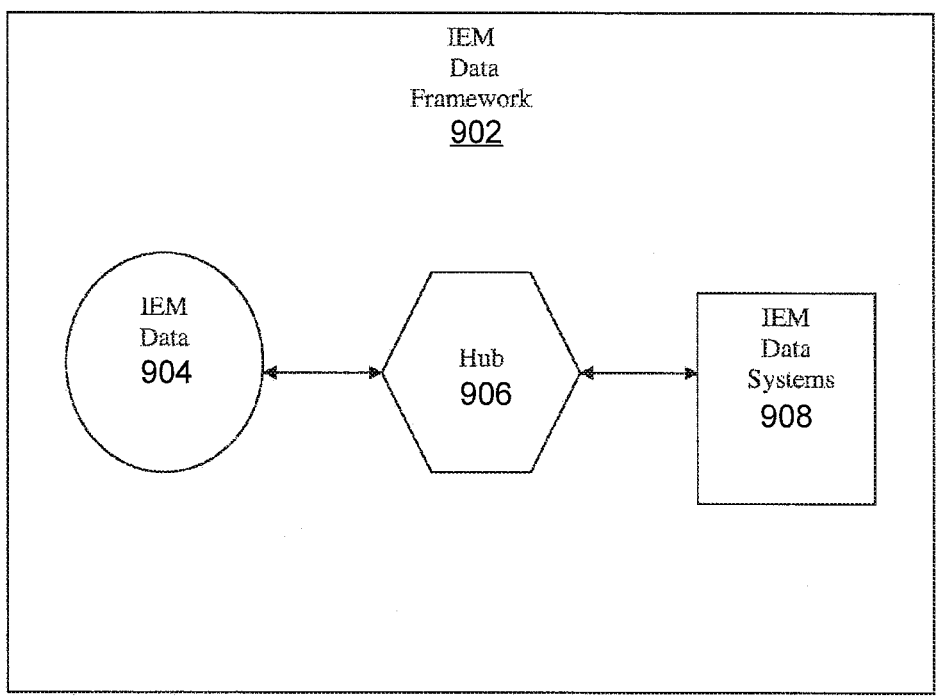

FIG. 9 provides a diagrammatic representation of an IEM data framework according to one aspect of the present disclosure.

Figure 10A:
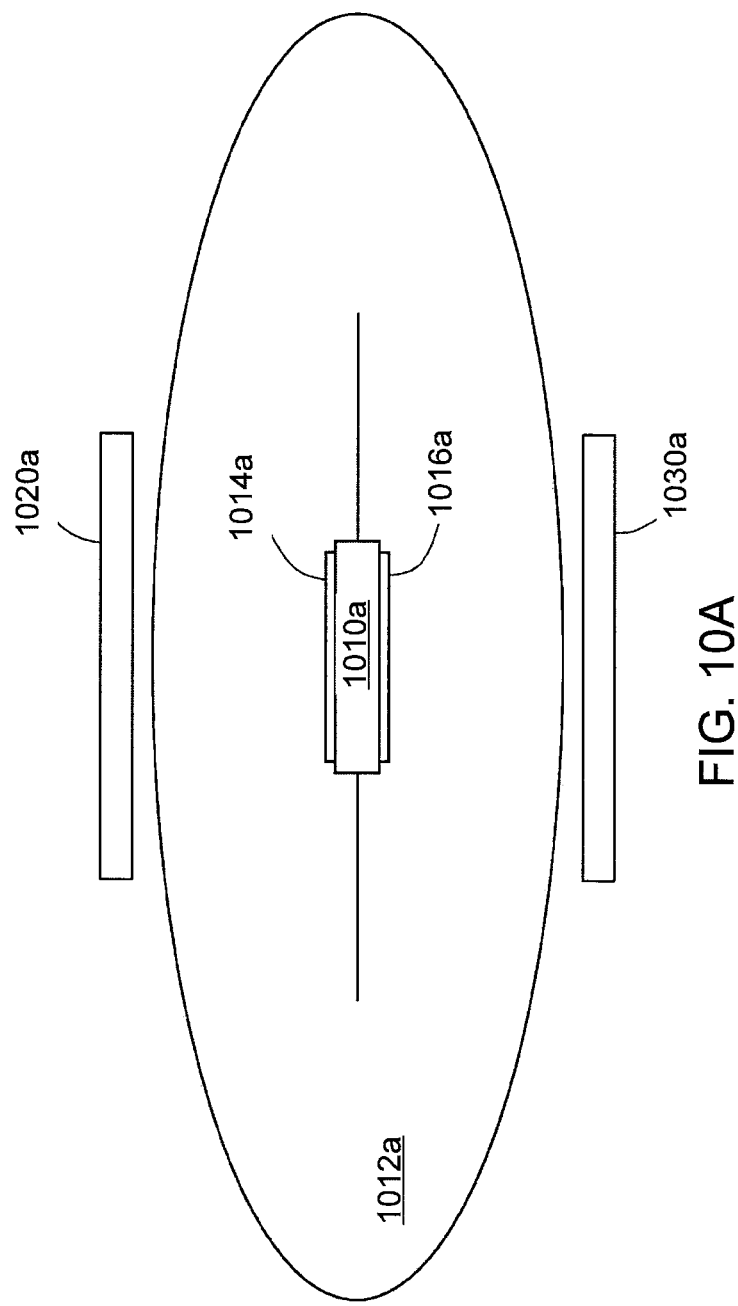

FIG. 10A shows a pharmaceutical product with an IEM that can be interrogated using capacitive coupling in accordance with one aspect of the present disclosure.

FIG. 10B shows a pharmaceutical product with an IEM that can be interrogated using capacitive coupling in accordance with another aspect of the present disclosure.

Figure 10C:
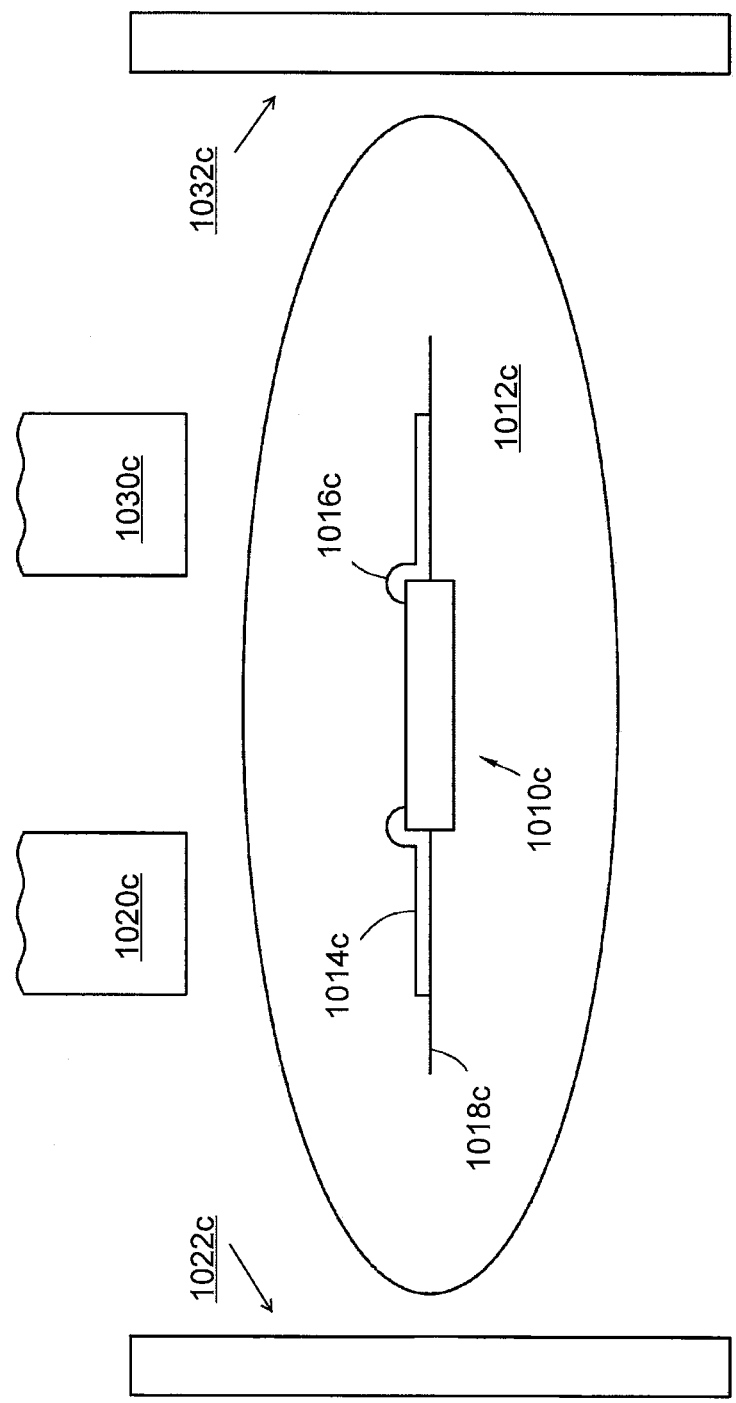

FIG. 10C shows a pharmaceutical product with an IEM that can be interrogated using capacitive coupling in accordance with another aspect of the present disclosure.

Figure 10D:
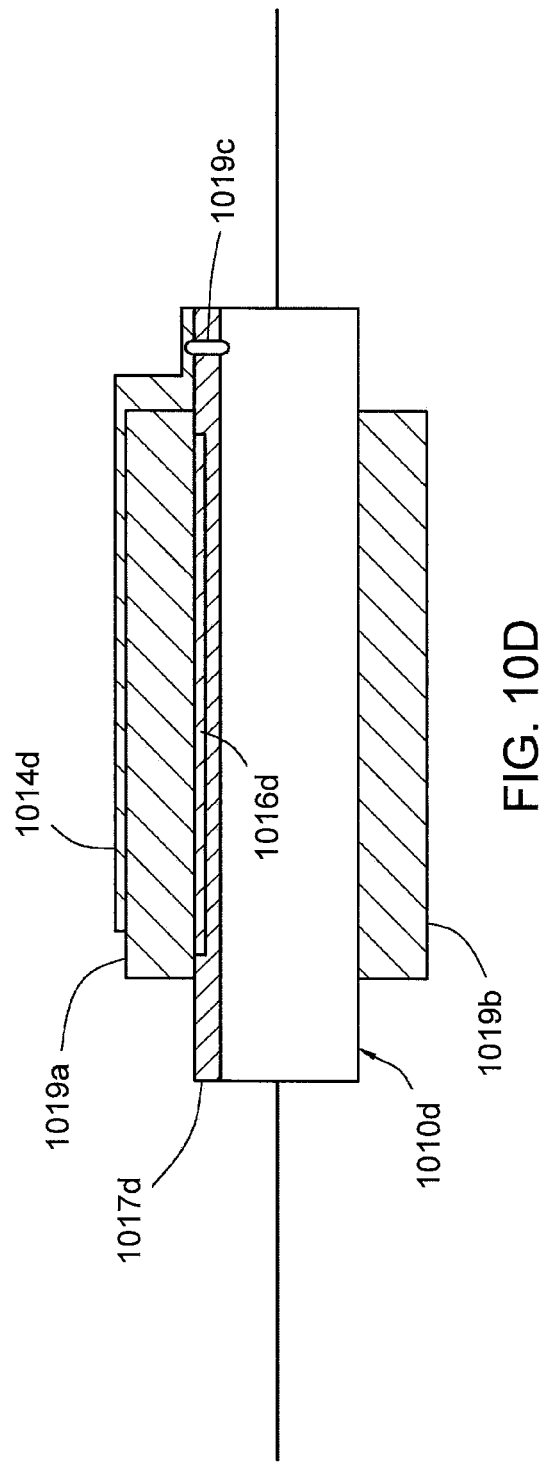

FIG. 10D shows an IEM that can be probed or interrogated using capacitive coupling in accordance with yet another aspect of the present disclosure.

FIG. 10E shows a pharmaceutical product with an IEM that can be probed or interrogated with a co-axial probe/plates using capacitive coupling in accordance with yet another aspect of the present disclosure.

Figure 11:
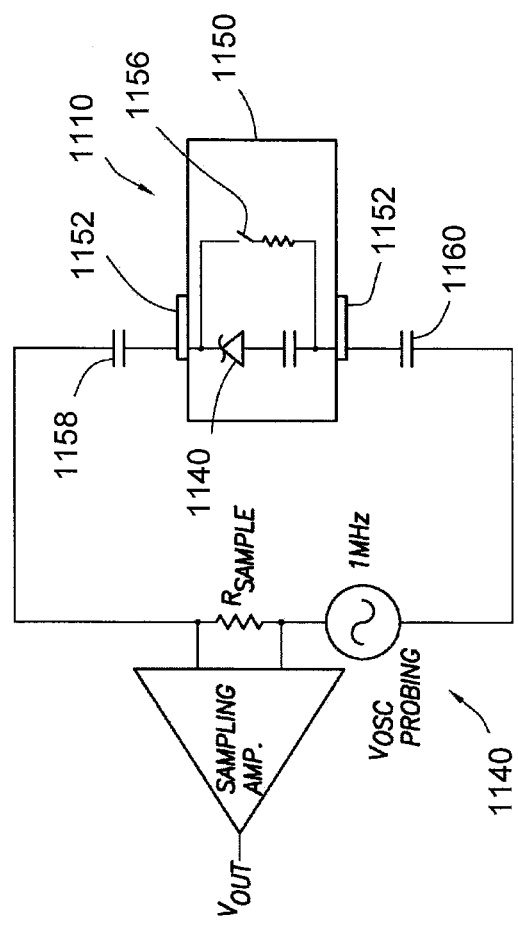

FIG. 11 shows an example circuit diagram for the IEMs of FIGS. 10A-10E in accordance with one aspect of the present disclosure.

FIG. 11A shows an example diode bridge usable in the IEM of FIG. 11.

FIG. 11B shows a logic unit of the IEM of FIG. 11 in communication with a probe through the plates and the conduction material, which is associated with the device in accordance with the present disclosure.

FIG. 11C shows a finite time period for a power transfer cycle and an information transfer cycle using capacitive coupling in accordance with the present disclosure.

Figure 12A:
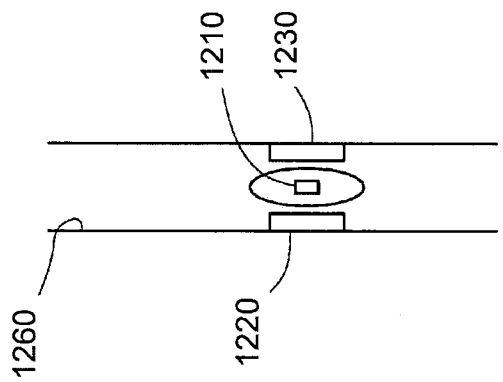

FIG. 12A shows an IEM device passing through a tubular section to confirm IEM device operation and to program/record a unique IEM identifier code in accordance with the present disclosure.

Figure 12B:
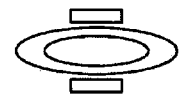

FIG. 12B is a specific instant of the IEM device passing between plates during interrogation/programming in accordance with the present disclosure.

Figures 13, 14:
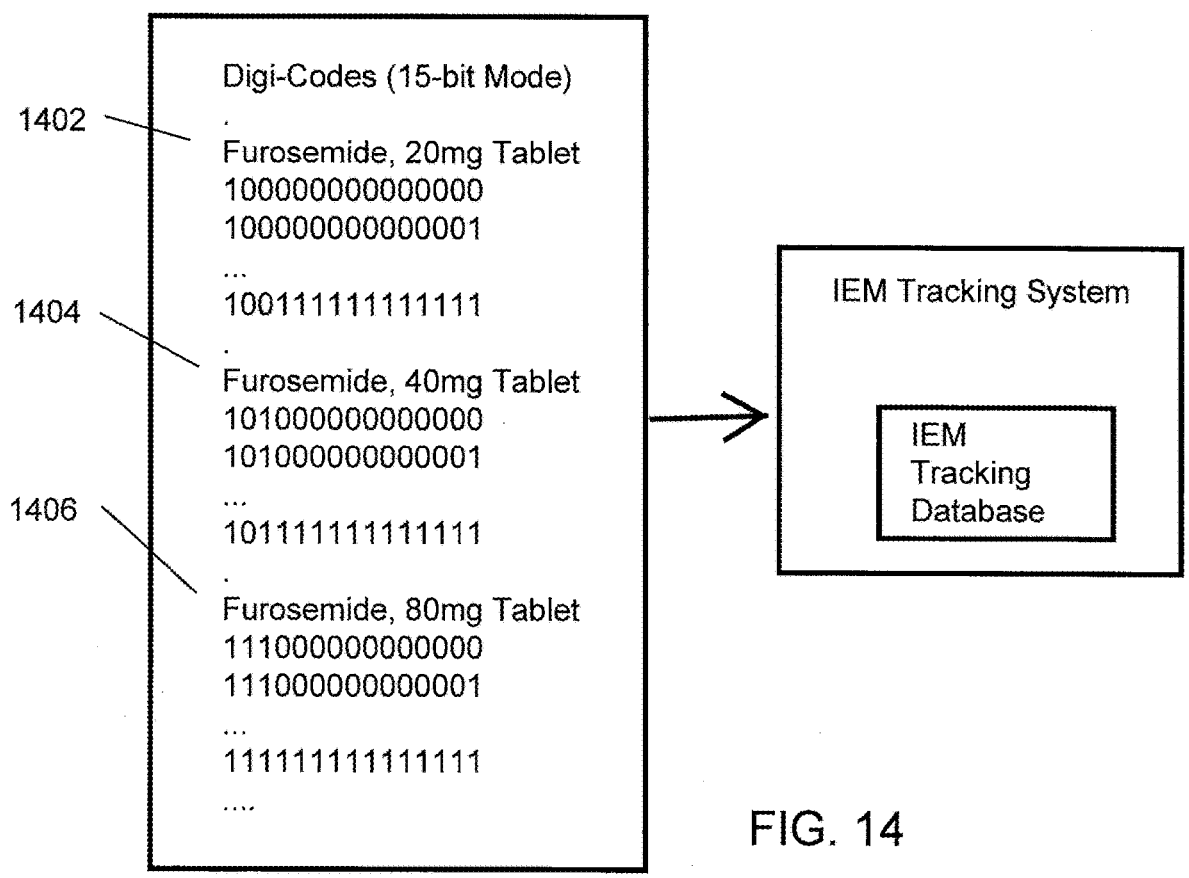

FIG. 13 illustrates example unique IEM identifier codes associated with a 15-bit Mode according to one aspect of the present disclosure.

FIG. 14 illustrates a digi-code block concept according to one aspect of the present disclosure.

Figure 15:
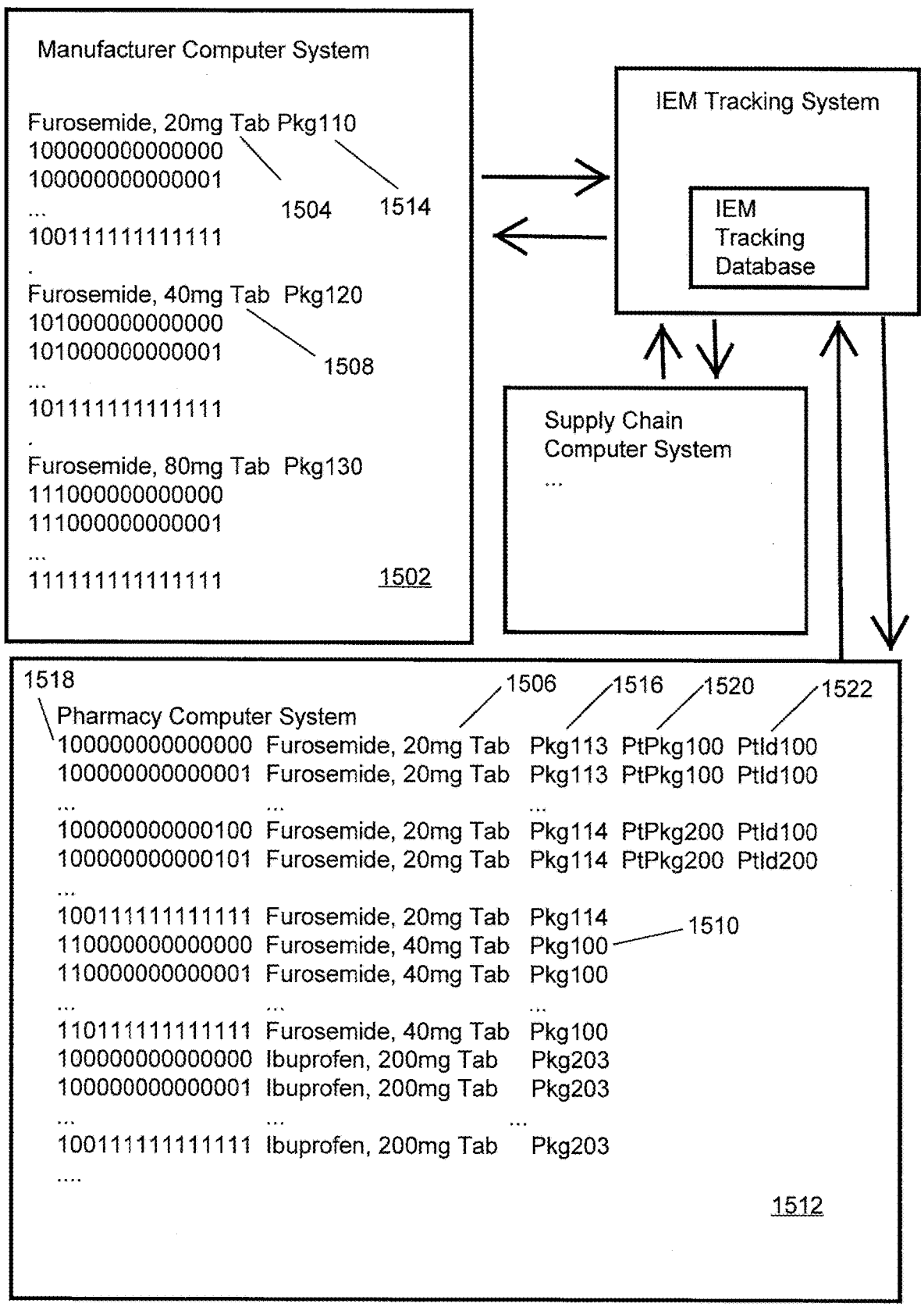

FIG. 15 illustrates example IEM data transfers between commercial systems and an IEM tracking system.

Figure 16:
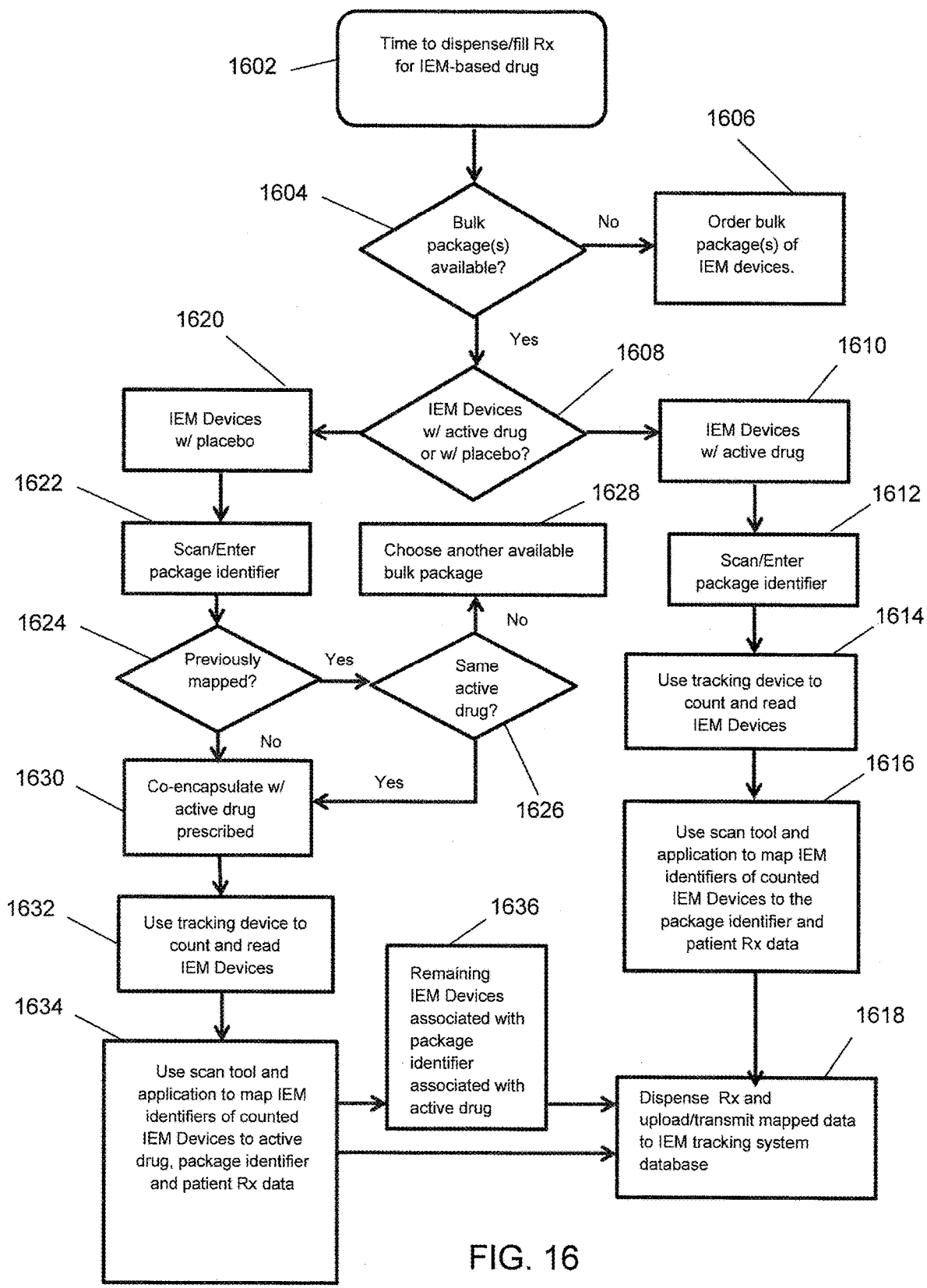

FIG. 16 illustrates a flow diagram for dispensing IEM devices at a pharmacy system according to one aspect of the present disclosure.

DETAILED DESCRIPTION

In the following detailed description, reference is made to the accompanying drawings, which form a part hereof. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented here.

Before explaining the various aspects of the present disclosure in detail, it should be noted that the various aspects disclosed herein are not limited in their application or use to the details of construction and arrangement of parts illustrated in the accompanying drawings and description. Rather, the disclosed aspects may be positioned or incorporated in other aspects, variations and modifications thereof, and may be practiced or carried out in various ways. Accordingly, aspects disclosed herein are illustrative in nature and are not meant to limit the scope or application thereof. Furthermore, unless otherwise indicated, the terms and expressions employed herein have been chosen for the purpose of describing the aspects for the convenience of the reader and are not to limit the scope thereof. In addition, it should be understood that any one or more of the disclosed aspects, expressions of aspects, and/or examples thereof, can be combined with any one or more of the other disclosed aspects, expressions of aspects, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings.

Problems to be Solved

Before getting into the details below, aspects of the present disclosure are intended to solve various problems including but not limited to: 1) problems associated with code mapping, 2) problems associated with code uniqueness and reuse, 3) problems associated with manufacturing complexity and buffer stocks, and 4) problems associated with regulatory risk.

With respect to code mapping, in order to be clinically useful as an aid to measure medication adherence, the identity of IEMs detected by a Proteus Digital Health Feedback Device (PDHFD) must be linked to the drug(s) of interest. This mapping of IEM digi-codes (individually programmed IEM identifier codes) to specific ingestion events (e.g., drug and dose form such as Furosemide, 20 mg) creates technical and business challenges.

With respect to code uniqueness and reuse, IEM digi-codes are limited in number. An IEM can be programmed during manufacture to operate in one of three modes, each with a different data payload length. One form (i.e., the most common) operates in 15-bit mode (15b). Another form operates in 30-bit mode (30b). Yet another form operates in 43-bit mode (43b). The mode of operation determines the number of unique identification codes available for IEM programming. In the 15-bit mode, for example, there are $2^{15}$ unique identification codes available (e.g., in a transistor memory, there are only two states, zero or one, so numbers are encoded as binary values). Since only 32,768 unique identification codes are available in the 15-bit mode, a reuse of digi-codes is a practical necessity.

With respect to manufacturing complexity and buffer stocks, in one aspect of the present disclosure, a digi-code block may be reserved for a particular medication dose form (e.g., Furosemide, 20 mg tablet) analogous to the way telephone numbers are reserved for a particular geographic region by use of area codes. However, hard-coding using digi-code blocks may raise a number of issues. For example, even if each MIT of a plurality of MITs is physically identical (e.g., an IEM incorporated into a placebo tablet), the plurality of physically identical MITs would effectively become multiple different products (e.g., segregated by reserved digi-code blocks). In such an aspect, a pharmacist asked to dispense IEM devices to aid in tracking patient adherence to a particular drug/medication could do so only if MITs hard-coded/programmed with digi-codes within a pre-defined digi-code block reserved for the particular drug/medication are in stock. In theory, a pharmacist could have multiple bottles of MITs available (e.g., hard-coded/programmed with digi-codes within pre-defined digi-code blocks reserved for other drugs/medications) but nonetheless be rendered incapable of filling a prescription. Such a division of physically identical MITs by pre-defined digi-code blocks may create manufacturing scale diseconomies, may dramatically escalate inventory requirements and supply chain complexity, and may increase the risk of not being able to satisfy customer demand.

With respect to regulatory risk, the FDA generally rules that medical devices referencing specific drugs require separate approval as drug-device combination products. This has been uncontroversial in the matter of manufacturing IEM devices (e.g., a drug substance containing an IEM, in the form of a drug tablet/pill or drug-containing capsule, etc.). In the case of Proteus, this may delay successfully realizing its existing cleared Indication for Use for the PDHFD, which implies the ability to discriminate between different ingested drugs by the patient (c.f., GlowCaps and other adherence-oriented devices and applications). In one aspect of the present disclosure, pharmacy-determined mapping of digi-codes to drug(s), as described herein, is a way to avoid this classification by FDA.

Prior to describing various solutions to the various problems revealed above, the present disclosure discusses topics including IEM Devices, Manufacturing IEM Devices, IEM Systems, and Communication Modes, as provided in headings herein. Such topics cover various systems, devices, processes, etc. that support Pharmacy Level Mapping and various other solutions disclosed herein.

IEM Devices

Various aspects of the present disclosure include an ingestible event marker device ("IEM device"). In one aspect, an IEM device may include an IEM directly combined with a composition (e.g., one or more drugs/medications) at the source of manufacture of the composition (e.g., the manufacturer/producer of a pharmaceutical composition) to become a drug-device combination. Such an IEM device can take the form of a drug tablet/pill or a drug-containing capsule. Such an IEM device may include an active agent composition having an IEM stably associated therewith. The active agent composition may include an active agent (e.g., a solid and/or liquid including an amount of active agent/drug, e.g., a dosage) and a pharmaceutically acceptable carrier/vehicle. The IEM itself may vary depending on the particular aspect and intended application of the composition. In certain aspects, the IEM is a component that emits a signal upon activation by a stimulus (e.g., by interrogation, upon contact with a target physiological location, etc.). As such, the IEM may emit a signal when it contacts a target body physiological site. In addition, or alternatively, the IEM may emit a signal when interrogated (e.g., via capacitive coupling, RFID, etc.).

In another aspect, an IEM device may include an IEM combined with a composition (e.g., one or more drugs/medications) in a pharmaceutically acceptable carrier/vehicle (e.g., capsule) by a licensed pharmacist (e.g. co-encapsulation). In such an aspect, the IEM itself may be combined with another composition (e.g., placebo/non-drug composition, etc.) at the source of manufacture (e.g., in the form a placebo tablet or MIT, e.g., to form a placebo/non-drug IEM device) prior to co-encapsulation by the pharmacist. In an alternative aspect, the IEM itself may be coated with a protective layer composition at the source of manufacture prior to co-encapsulation by the pharmacist. In various aspects, the placebo, non-drug, and/or protective layer compositions may preserve the IEM and components thereof prior to co-encapsulation by the pharmacist (e.g., after manufacture, during transit to the pharmacy, while in inventory, etc.). Again, the IEM may vary depending on the particular aspect and intended application of the composition. In certain aspects, the IEM is a component that emits a signal upon activation by a stimulus (e.g., by interrogation, upon contact with a target physiological location, etc.). As such, the IEM may emit a signal when it contacts a target body physiological site. In addition, or alternatively, the IEM may emit a signal when interrogated (e.g., via capacitive coupling, RFID, etc.).

In various aspects of the present disclosure, the signal emitted by the IEM may be a unique signal (e.g., a signal which in some way uniquely identifies that a particular composition associated with the IEM has contacted the target physiological site). Such a unique signal is distinguishable from other signals emitted by IEMs associated with other compositions of a plurality of compositions at the target physiological site. In various aspects, the IEM may emit a signal that uniquely identifies a given unit dosage, even from other identical unit dosages, in a given batch. Accordingly, in certain aspects the IEM may emit a unique signal that distinguishes a given type of unit dosage from other types of unit dosages, e.g., a given medication from other types of medications. In certain other aspects, the IEM may emit a unique signal that distinguishes a given unit dosage from other unit dosages of a defined population of unit dosages, e.g., a prescription, a batch or a lifetime production run of dosage formulations. In certain aspects, the IEM may emit a signal that is unique, i.e., distinguishable, from a signal emitted by any other dosage formulation ever produced, where such a signal may be viewed as a universally unique signal (e.g., analogous to a human fingerprint which is distinct from any other fingerprint of any other individual and therefore uniquely identifies an individual on a universal level). In one aspect, the signal may either directly convey information about the composition, or provide an identification code, which may be used to retrieve information about the composition from a database, e.g., a database linking identification codes with compositions (e.g., an IEM tracking system database discussed herein).

The IEM may be any component or device that is capable of generating a detectable signal following activation in response to a stimulus. In certain aspects, the stimulus activates the IEM to emit a signal once the composition comes into contact with a physiological target site. For example, a patient may ingest an IEM device including an IEM, wherein the IEM upon contact with gastrointestinal/stomach fluids, generates a detectable signal. Depending on the application, the target physiological site or location may vary. Example target physiological sites include, but are not limited to: a location in the gastrointestinal tract (e.g., mouth, esophagus, stomach, small intestine, large intestine, etc.); an alternative location inside the body (e.g., a parental location, vascular location, etc.); a topical location; etc.

Figure 6:
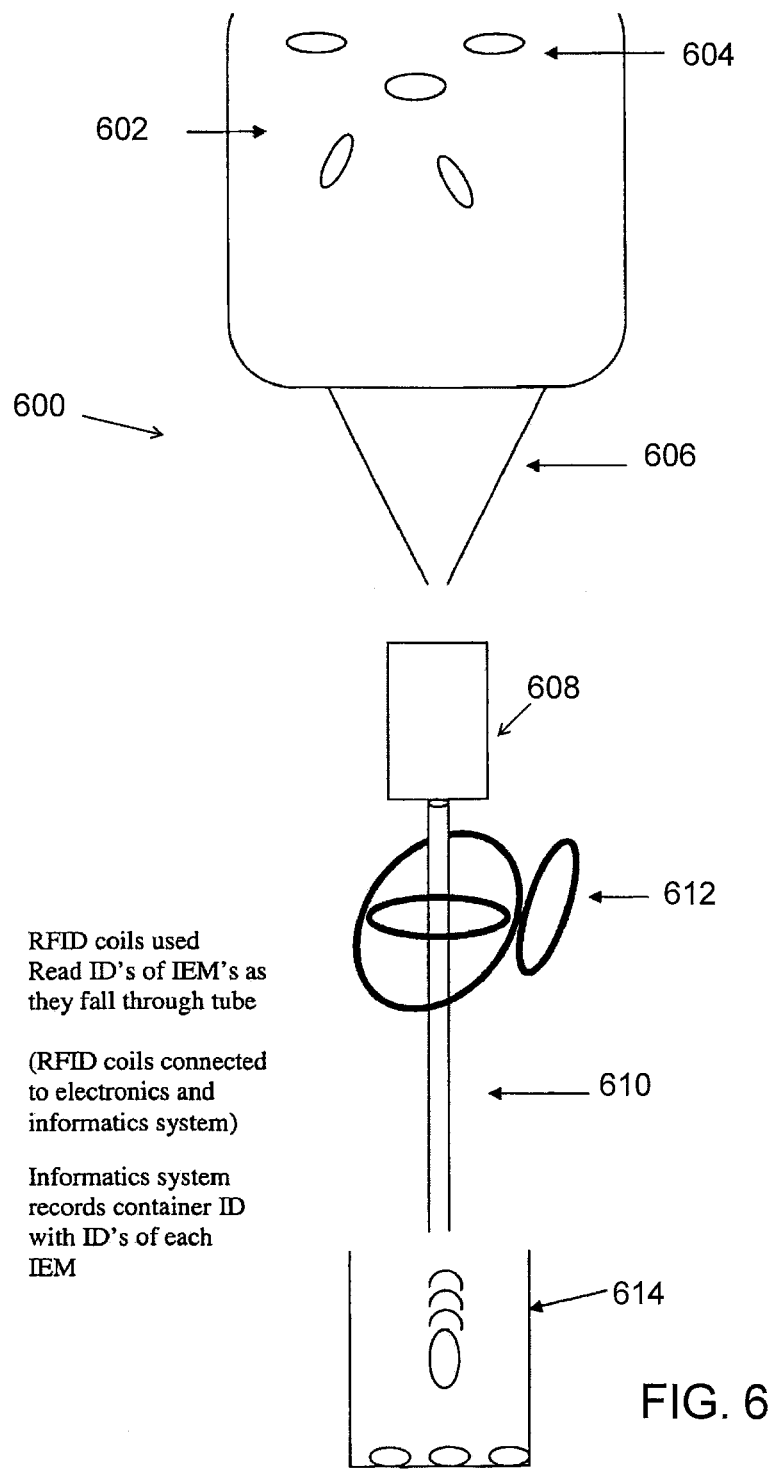
FIG. 6 shows a tracking device that may be used in a commercial system according to one aspect of the present disclosure.
Figure 8:
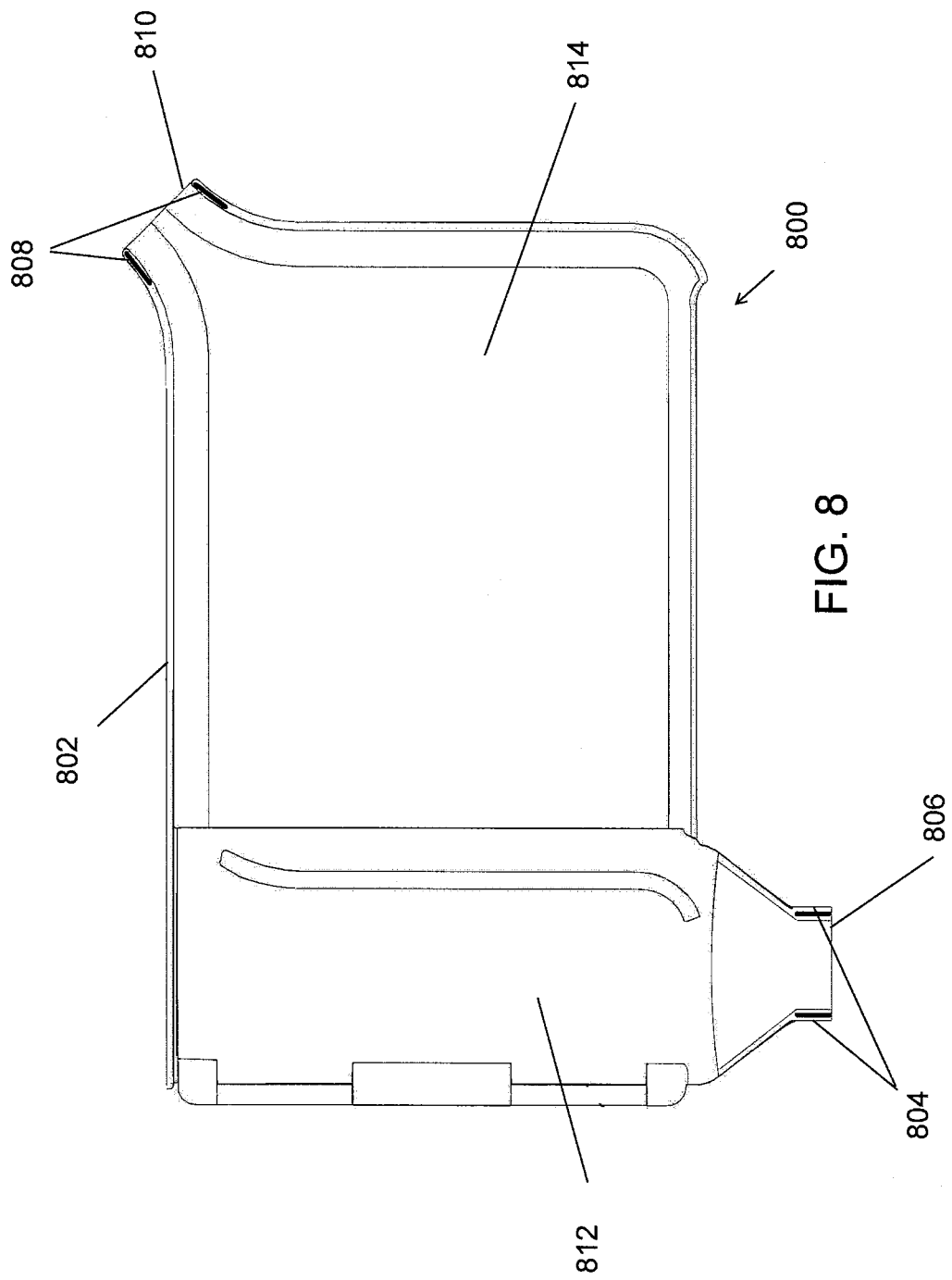
FIG. 8 shows a tracking device that may be used in a commercial system, according to one aspect of the present disclosure.

In certain aspects the stimulus that activates the IEM may be an interrogation signal, such as a scan or other type of interrogation (See e.g., FIG. 6, showing, e.g., RFID coils, FIG. 8, capacitive coupling, a wand/scan tool, etc.). In such aspects, the stimulus activates the IEM, thereby emitting a signal which is then received and processed, e.g., to identify the composition (e.g., directly or via a query of an IEM tracking system database).

The IEM may generate a variety of different types of signals, including but not limited to, RF, magnetic, conductive (near field), acoustic, etc.

In one aspect, the IEM may be one that is hard-coded/programmed during manufacture of the IEM. In such an aspect, a plurality (e.g., hundreds/thousands) of individual integrated circuits (e.g., each associated with an IEM) may be present on a wafer during wafer processing. In such an aspect, the wafer is moved into contact with a probe card of a wafer prober. When microscopic probes of the probe card are in contact with each integrated circuit, the wafer prober may test each integrated circuit for functional defects in a testing phase and may program each integrated circuit in a programming phase. Subsequent to testing and programming, each individual integrated circuit may be separated from the wafer using a dicing process. In one aspect of the present disclosure, the wafer prober may, in the programming phase, hard-code each integrated circuit with a unique identification code. In various aspects, the unique identification code may be stored in a memory component of the integrated circuit (e.g., non-volatile random-access memory). In various aspects, the unique identification code may include a digi-code as discussed herein. In various aspects of the present disclosure, the manufacturer of the IEMs may transmit the hard-coded/programmed unique IEM identifier codes to an IEM tracking system (discussed herein).

In an alternative aspect, the IEM may be one that is programmable following manufacture, in the sense that the signal generated by the IEM may be determined after the IEM is produced, where the IEM may be field programmable, mass programmable, fuse programmable, and even reprogrammable. Such an aspect may be of interest where IEMs are first produced and following incorporation into a composition (e.g., IEM device) are then coded to emit an identifying signal for that composition. Any convenient programming technology may be employed. In certain aspects, the programming technology employed is RFID technology (e.g., smart tag technology). With RFID or another programming technology, an entity (e.g., manufacturer, vendor, pharmacy, etc.) may associate a unique identification code (e.g., IEM identifier code) with a given IEM, even after the IEM has been incorporated into a composition. In certain aspects, each individual or entity involved in the handling of the composition prior to use may introduce information into the IEM, e.g., in the form of programming with respect to the signal emitted by the IEM. See e.g., FIG. 5, reference 518. Such an aspect, however, may not be preferred. For example, if an IEM were programmable/reprogrammable following manufacture an entity (e.g., patient) could program/reprogram a first IEM device (by programming/reprogramming an IEM stably associated with composition "A", e.g., Ibuprofen, placebo, etc.) to mimic a second IEM device (e.g., an IEM stably associated with composition "B", e.g., Furosemide). More specifically, for example, the entity could program/reprogram the IEM of the first IEM device with a unique identification code read from the IEM of the second IEM device in the patient's prescription. In such an instance, when the patient ingests the first IEM device (e.g., including Ibuprofen, a placebo, etc.) the unique identification code of the second IEM device (e.g., associated with Furosemide) would ultimately be transmitted to the IEM System. Absent further security measures, the patient could theoretically trick the IEM system into determining that the patient has adhered by ingesting their prescribed composition (e.g., Furosemide) when the patient has actually ingested a different composition (e.g., Ibuprofen, placebo, etc.).

In various aspects, it may be desired that an IEM be one that is not programmable/reprogrammable after manufacture (e.g., when monitoring drug/medication adherence). Such an aspect may be suitable if fraudulent programming/reprogramming may occur. For example, utilizing IEMs that are not programmable/reprogrammable following manufacture would inhibit an entity (e.g., a patient) from programming/ reprogramming a first IEM device to mimic a second IEM device including a drug/medication that the patient is prescribed to take. More specifically, the entity could not program/reprogram the IEM of the first IEM device with another unique identification code (e.g., including one read from the IEM of the second IEM device in the patient's prescription). In such an instance, when the patient ingests the first IEM device, the unique identification code of the first IEM device is ultimately transmitted to the IEM system and when the patient ingests the second IEM device, the unique identification code of the second IEM device is ultimately transmitted to the IEM system. The patient could not trick the IEM system into determining that the patient has adhered by ingesting their prescribed composition (e.g., Furosemide) when the patient has actually ingested a different composition (e.g., Ibuprophen, placebo, etc.).

The IEM in certain aspects includes a memory element, where the memory element may vary with respect to its capacity. In certain aspects, the memory element has a capacity ranging from about 1 bit to 1 gigabyte or more, such as 1 bit to 1 megabyte, including from about 1 bit to about 128 bit. The particular capacity employed may vary depending on the application, e.g., where the signal is a coded signal, where the signal may be annotated with additional information (e.g., a unique patient identifier), etc.

IEM components, according to aspects of the present disclosure, include: (a) an activation component (e.g., battery completion) and (b) a signal generation component, where the signal generation component is activated by the activation component to produce an identifying signal, e.g., as described above.

In one aspect of the present disclosure the activation component may be by battery completion. In such an aspect, the battery includes, when completed, a cathode, an anode, and an electrolyte. When the IEM device (e.g., IEM stably associated with an active agent composition) is administered (e.g., ingested) and travels through the esophagus, it proceeds to enter the stomach. A cathode and an anode provided within the IEM do not constitute a full battery. However, as the active agent composition dissolves to expose the cathode and anode of the IEM, stomach fluid (e.g., hydrochloric acid and other digestive agents) acts as the electrolyte component of the battery. The added component of the stomach fluid thus completes the battery. Therefore, when the IEM device contacts the target site, e.g., by entering the stomach and dissolving to the point of cathode and anode exposure, a power source is provided which activates the IEM, e.g., in chip configuration. The data signal (e.g., described herein) is then transmitted by the IEM identifier.

Figure 1:
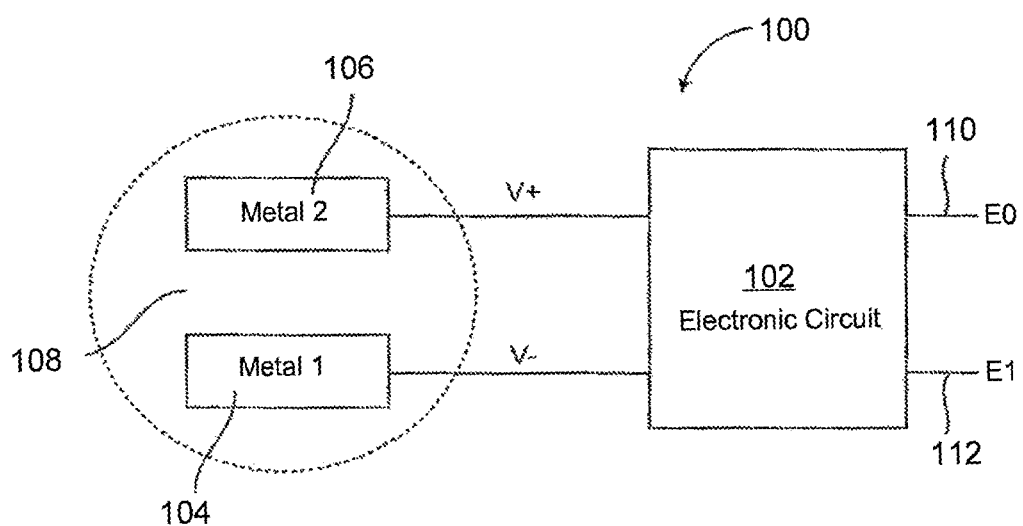
FIG. 1 shows an example IEM battery according to one aspect of the present disclosure.

FIG. 1 illustrates an IEM 100 having a signal generation element 102 powered by reverse electrolysis. In one aspect the signal generation element 102 includes an electronic circuit. Signal generation element 102 is electrically connected to metal electrodes 104 and 106, which are made of two different materials and are electrically insulated from each other. When metal electrodes 104 and 106 are immersed in an ionic solution 108, a potential difference develops between them. For instance, electrode 106 rises to a higher potential V+ while electrode 104 falls to a lower potential V−. This potential difference can be used to power a signal generation element/electronic circuit 102. The two outputs of that electronic circuit 102 are E0 110 and E1 112, which are the signal-transmission electrodes on the top surface. In an alternate aspect (not shown) the IEM may include a single-transmission electrode, e.g., output E0 110.

Electrodes 104 and 106 can be implemented in various ways; for instance, areas on opposing surfaces of an integrated circuit (IC) chip can be coated with two different metals, and the entire IC chip can be placed in the ionic solution. Electrodes 104 and 106 can be made of any two materials appropriate to the environment in which the IEM 100 will be operating. For instance, in some aspects where the ionic solution 108 includes stomach acids, electrodes 104 and 106 may be made of a noble metal (e.g., gold, silver, platinum, palladium or the like) so that they do not corrode prematurely. In an alternative aspect, the electrodes 104 and 106 can be fabricated of aluminum or any other conductive material whose survival time in the applicable ionic solution is long enough to allow the IEM 100 to perform its intended function.

A variety of different materials may be employed as the battery electrodes 104 and 106 (e.g., CuCl or CuI, etc., as the cathode; and Mg or Zn, etc., as the anode). In certain aspects, electrode materials are chosen to provide a voltage upon contact with the target physiological site, e.g., the stomach, sufficient to drive a signal generation element 102 of the IEM. In certain aspects, the voltage provided by the electrode materials upon contact with the target physiological site is 0.001 V or higher, including 0.01 V or higher, such as 0.1 V or higher, e.g., 0.3 V or higher, including 0.5 volts or higher, and including 1.0 volts or higher. In certain aspects, the voltage ranges from about 0.001 to about 10 volts, such as from about 0.01 to about 10 V.

In certain aspects, the signal generation element 102 includes circuitry, as developed in more detail below, which produces or generates the signal. The type of circuitry chosen may depend, at least in part, on the driving power that is supplied by the power source/battery of the IEM. For example, where the driving power is 1.2 volts or above, standard CMOS circuitry may be employed. In other aspects where the driving power ranges from about 0.7 to about 1.2 V, sub-threshold circuit designs may be employed. For driving powers of about 0.7 V or less, zero-threshold transistor designs may be employed.

In certain aspects, the signal generation element 102 includes a voltage-controlled oscillator (VCO) that can generate a digital clock signal in response to activation by the activation component. The VCO can be controlled by a digital control circuit, which is assigned an address and which can control the VCO with a control voltage. This digital control circuit can be embedded onto an IC chip that includes the activation component and oscillator. Using amplitude modulation or phase shift keying to encode the address, an identifying signal is transmitted.

Figure 2:
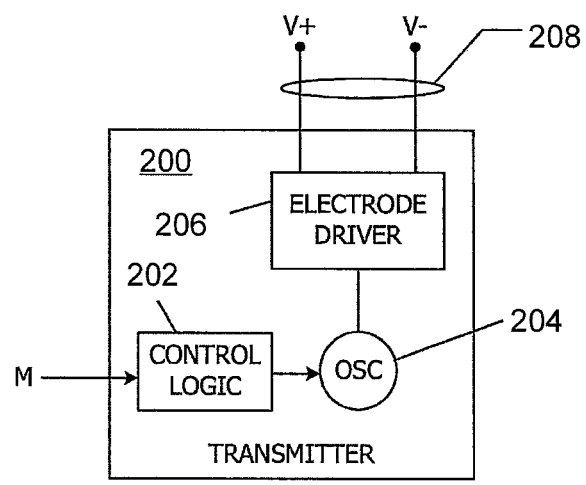
FIG. 2 illustrates and example IEM circuit according to one aspect of the present disclosure.

FIG. 2 is a block diagram of a signal generation element 200 for an IEM according to an aspect of the present disclosure. In various aspects, the signal generation element 200 includes a transmitter. Referring to FIG. 2, the signal generation element 200 receives a signal M from an activation component which activates the signal generation element 200 to produce and emit a signal. Signal generation element 200 includes control logic 202, an oscillator 204, an electrode driver 206, and an antenna 208 (in this instance, a pair of electrodes operated as an electric dipole antenna). In operation, oscillator 204 generates an oscillating signal (e.g., waveform) in response to signals from control logic 202. The signals from control logic 202 can start or stop the oscillator and in some aspects can also shape one or more aspects of the oscillatory signal such as amplitude, frequency, and/or phase. Oscillator 204 provides the waveform to electrode driver 206, which drives current or voltage on antenna 208 to transmit a signal into the conductive medium of body tissues and/or fluids.

Depending on a given aspect, the signal may or may not be modulated. For example, in certain aspects the frequency of the signal may be held constant. Referring to FIG. 2, for example, oscillator 204 may operate at a constant frequency. The receipt of a constant-frequency signal in and of itself can provide useful information, e.g., that a remote device is present and operational. In yet other aspects, the signal may be modulated in some manner, e.g., via carrier based modulate schemes, ultra-wide band (or time domain based) modulation schemes, etc. Oscillator 204, for example, may modulate its signal to encode additional information.

Information can be encoded in various ways, generally by modulating (varying) some property of the transmitted signal, such as frequency, amplitude, phase, or any combination thereof. Modulation techniques known in the art may be employed.

In general, information can be transmitted using analog or digital techniques. Analog techniques refer generally to instances in which the modulated property is varied in different degrees, with the degree of variation being correlated to a value representing the information to be transmitted. For instance, suppose that the signal generation element 200 is transmitting a signal. Oscillator 204 can be designed to operate over some range of frequencies. Digital techniques refer generally to instances in which the information to be transmitted is represented as a sequence of binary digits (bits), and the signal is modulated based on the bit stream. For instance, suppose again that the signal generation element 200 is transmitting a signal using digital techniques. Oscillator 204 can be designed to operate at least two different frequencies, with one frequency corresponding to bit value 0 and another frequency corresponding to bit value 1. In aspects of the present disclosure, either analog techniques, digital, techniques, or a combination thereof can be used to transmit information. In addition, various types of modulation may be implemented.

In one aspect, frequency modulation may be used. Oscillator 204 can be a voltage-controlled oscillator (VCO), an oscillator circuit in which the oscillation frequency depends on an applied voltage. Control logic 202 supplies an appropriate voltage (e.g., reflecting the value of the measurement data, M), and the frequency of the signal indicates the value of the data. In another aspect, amplitude modulation may be used. For example, the amplitude of the driving signals φ and /φ can be varied, or the positive and negative rails of the driver circuit (e.g., V+ and V−) can be varied to control the amplitude. In yet another aspect, phase modulation may be used. For example, in digital signal transmission, one phase corresponds to bit value 0, an opposite phase corresponds to bit value 1, and the phase shifts represent transitions. Oscillator 204 can include a switch circuit that either directly connects or cross-connects the driving signals φ and /φ to the inputs of a driver circuit. Combinations of frequency modulation, amplitude modulation, and/or phase modulation may also be used as desired.

In various aspects, the signal generation element 200 may transmit a "packet" that includes a unique identifier (e.g., an IEM identifier code, a digi-code, etc.) for the IEM, which in turn is for the composition with which the IEM is associated. As discussed herein, such an IEM identifier code may have been pre-programmed to the IEM when manufacturing the IEM. The IEM identifier code may also provide access to additional information located on a remotely located device (e.g., the identity of the active agent, annotation information). In one aspect, such additional information may be accessed by querying a remote IEM tracking system database using the IEM identifier code transmitted in the packet.

Other techniques for distinguishing different signals may also be used, including: operating different transmitters in different frequency bands, allowing each transmitter to be identified by its frequency and/or configuring different transmitters to transmit at different (and known) times, allowing the transmitter to be identified by when it transmits.

Figure 3A:
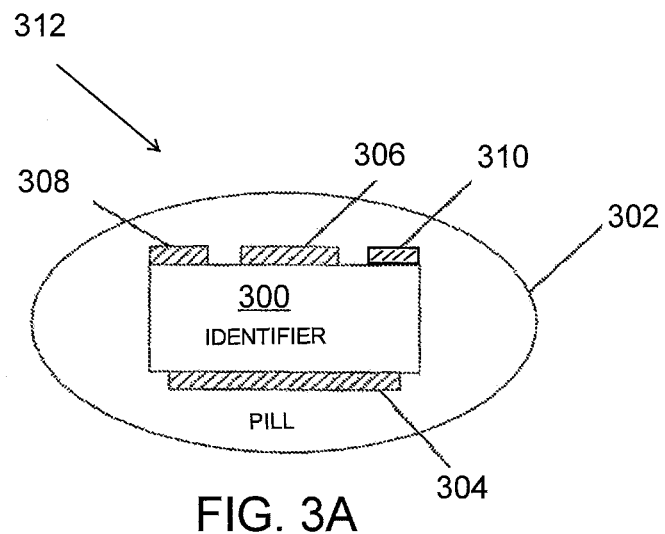
FIGS. 3A and 3B illustrate a detailed view of a pill composition.
Figure 3B:
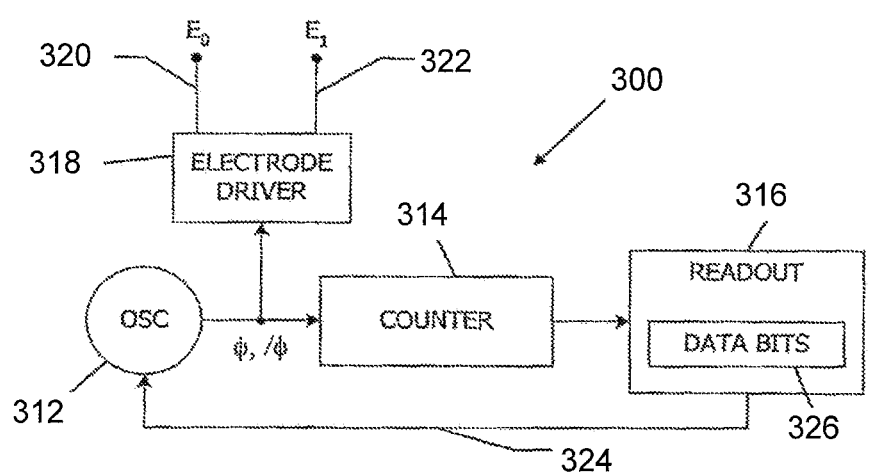

FIGS. 3A and 3B provide a more detailed view of a tablet/pill composition 312. FIG. 3A illustrates an IEM 300 disposed inside a tablet/pill 302. The IEM 300 may be present as an integrated circuit (IC). Referring to FIG. 3A, the bottom surface of the IEM 300 is at least partially coated with a first metal 304, and a portion of the top of the IEM 300 is coated with a different metal 306, allowing the IEM 300 to be powered by reverse electrolysis, e.g., as described above. Also on the top surface are two transmitter electrodes 308 and 310.

As discussed above, in one aspect, FIG. 3A may depict an IEM 300 directly combined with a composition (e.g., one or more drugs/medications) at the source of manufacture of the composition (e.g., the manufacturer/producer of a pharmaceutical composition) to become a drug-device combination (e.g., a drug tablet/pill). In such an aspect, the "drug" composition may dissolve in the stomach through a combination of the mechanical action of the stomach and the action of various chemical constituents (e.g., hydrochloric acid) in stomach fluids. In another aspect, FIG. 3A may depict an IEM combined with a "first" composition (e.g., placebo/inert composition, non-drug composition, and/or protective layer composition, etc.) at the source of manufacture (e.g., in the form a placebo tablet or MIT). Such an IEM may be subsequently combined with a "drug" composition (e.g., one or more drugs/medications) in a pharmaceutically acceptable carrier/vehicle (e.g., capsule) by a licensed pharmacist (e.g. co-encapsulation). See e.g., FIG. 4, references 418 and 422. In such an aspect the pharmaceutically acceptable carrier/vehicle, the "drug" composition, and the "first" composition may dissolve in the stomach through a combination of the mechanical action of the stomach and the action of various chemical constituents (e.g., hydrochloric acid) in stomach fluids.

As the tablet/pill composition 312 is dissolved, areas of the IEM 300 become exposed to the stomach contents, which for present purposes can be regarded as an electrolyte solution. As dissolution of the tablet/pill composition 312 exposes metal layers 304 and 306, power is supplied to the IC of the IEM 300, which begins to operate and continues to operate until metal layers 304 and 306 or the circuit itself are sufficiently dissolved by digestive processes and acids to become non-functional. When power is supplied, the IEM 300 may transmit its identifying signal (e.g., IEM identifier code) via transmitter electrodes 308 and 310. Eventually, any remains of the IEM 300 are naturally excreted from the body.

In an alternative aspect, the IEM 300 may be attached to, rather than encapsulated within, the tablet/pill 302. For instance, the IEM 300 might be placed at one end of the tablet/pill 302 as the tablet/pill 302 is being prepared, in a soluble coating on a surface of the tablet/pill 302, or the like. In various aspects, the IEM 300 may be wholly or partially exposed. In such aspects the IC of the IEM 300 may begin to operate sooner after the tablet/pill 302 enters the stomach rather than after the tablet/pill 302 dissolves. Similar to above, when power is supplied, the IEM 300 may transmit its identifying signal (e.g., IEM identifier code) via transmitter electrodes 308 and 310.

FIG. 3B is a block diagram of one aspect of the IC of the IEM 300. In this aspect, the IEM 300 is a transmitter configured/programmed to sequentially transmit a series of address (identifier) bits 326 using frequency shift keying, with a first oscillation frequency corresponding to bit value 0 and a second oscillation frequency corresponding to bit value 1. As described above, the metal layers 304 and 306 supply power to the IC of the IEM 300. The power is supplied to an oscillator 312, a counter 314, a readout circuit 316, and an electrode driver 318 that drives transmitter electrodes 320 and 322 to transmit the signal. Oscillator 312 may be of general conventional design (e.g., a ring oscillator) and is advantageously configured to operate in a quasi-electrostatic frequency region. Oscillator 312 generates a driving signal $\varphi$ that oscillates between high and low voltage levels and an inverted driving signal $/\varphi$ that is opposite in phase to driving signal $\varphi$. In one aspect, oscillator 312 is a voltage-controlled oscillator (VCO) with an oscillation frequency that depends on a control voltage provided on a signal path 324. Counter 314 counts the oscillations of driving signals $\varphi$ and $/\varphi$ and provides the current count to readout circuit 316. In one aspect, counter 314 is an 8-bit counter of general conventional design; other types of counters (including counters with different widths) may also be used. As discussed above, the readout circuit 316 is configured with a set of address (identifier) bits 326 that may be fixed, e.g., at the time the IEM 300 is manufactured/fabricated. Further, as noted above, the bits can be unique to a particular instance of the tablet/pill 302. In one aspect, pills containing a same particular pharmacological agent may be assigned a set of address (identifier) bits including a digi-code associated with the particular pharmacological agent (discussed further below). Address bits 326 can be stored in nonvolatile storage circuits of generally conventional design, and any number of address bits (e.g., 8, 15, 16, 30, 32, 43, 48, etc.) may be provided. Readout circuit 316 generates an oscillator control signal (e.g., a voltage) on line 324 that controls the frequency of VCO 312. In one aspect, readout circuit 316 is configured to select a current address bit, e.g., based on the current count provided by counter 314, and to generate a control signal on signal line 324 that selects a frequency corresponding to the value of that bit (i.e. "1" or "0"). After some number of cycles (as determined by counter 314), readout circuit 316 selects the next address bit and generates the corresponding control voltage on signal line 324. Various frequencies may be used to represent the address bit values "1" and "0." In one aspect, frequencies of 100 kHz and 200 kHz may be used to represent values "0" and "1," respectively. Other values (e.g., 1 MHz and 2 MHz or 1 kHz and 5 kHz) may also be used. The chosen frequencies may be well below the absorption modes of human tissues, which are typically above 400 MHz. As described above, VCO 312 generates complementary signals $\varphi$, $/\varphi$ that oscillate at a frequency determined by the control signal on signal line 324. The signals $\varphi$, $/\varphi$ are used to control an electrode driver 318. It should be noted that since electrodes 304 and 306 are in contact with stomach fluids when the IC of the IEM 300 is operative, the near-field component is coupled directly into the conductive medium of the patient's body and can be detected by a suitably configured receiver (discussed below). In one aspect, the receiver is configured to log the received address (e.g., unique identifier code, digi-code) and the time of receipt. The receiver can also be configured to retransmit this information to an external device (e.g., IEM tracking system), either in real time or while the patient is in a medical facility. It will be appreciated that the transmitter described herein is illustrative and that variations and modifications are possible. For instance, other encoding schemes could be used to transmit the data; in one such aspect, phase shift keying rather than frequency keying is used. In some aspects, multiple address bits can be encoded into a single symbol that is transmitted using various keying schemes known in the art.

The signal generation element (e.g., FIG. 1, 102, FIG. 2, 200, FIG. 3A, 300) of the IEM is a structure that, upon activation by the activation component, emits a detectable signal, e.g., that can be received by a receiver. The signal generation element of certain aspects can be any convenient device that is capable of producing a detectable signal and/or modulating transduced broadcast power, upon activation by the activation component. Detectable signals of interest include, but are not limited to: conductive signals, acoustic signals, RF signals, etc. Representative types of signals of interest include, but are not limited to: frequency shift coded signals; amplitude modulation signals; frequency modulation signals, etc.

Such IEM devices may be utilized to automatically detect and identify pharmaceutical agents actually delivered to a consumer patient's body. Various IEM devices including IEMs are discussed in U.S. Pat. No. 8,847,766, entitled "Pharma-Informatics System", U.S. Provisional Application Ser. No. 60/790,335, entitled "Pharma-Informatics System", U.S. Provisional Application Ser. No. 60/713,680, entitled "Medical Diagnostic and Treatment Platform Using Near-Field Wireless Communication of Information Within a Patient's Body", U.S. Provisional Application Ser. No. 60/694,078, entitled "Pharma-Informatics System", and U.S. Provisional Application Ser. No. 60/676,145, entitled "Pharma-Informatics System", the entire disclosures of which are hereby incorporated by reference herein.

Manufacturing IEM Devices

Various systems/methods may be used to manufacture an IEM device. Example systems/methods include those discussed in U.S. Patent Application Publication No. 2012/0011699, entitled "High-Throughput Production of Ingestible Event Markers", the entire disclosure of which is hereby incorporated by reference herein.

Figure 4:
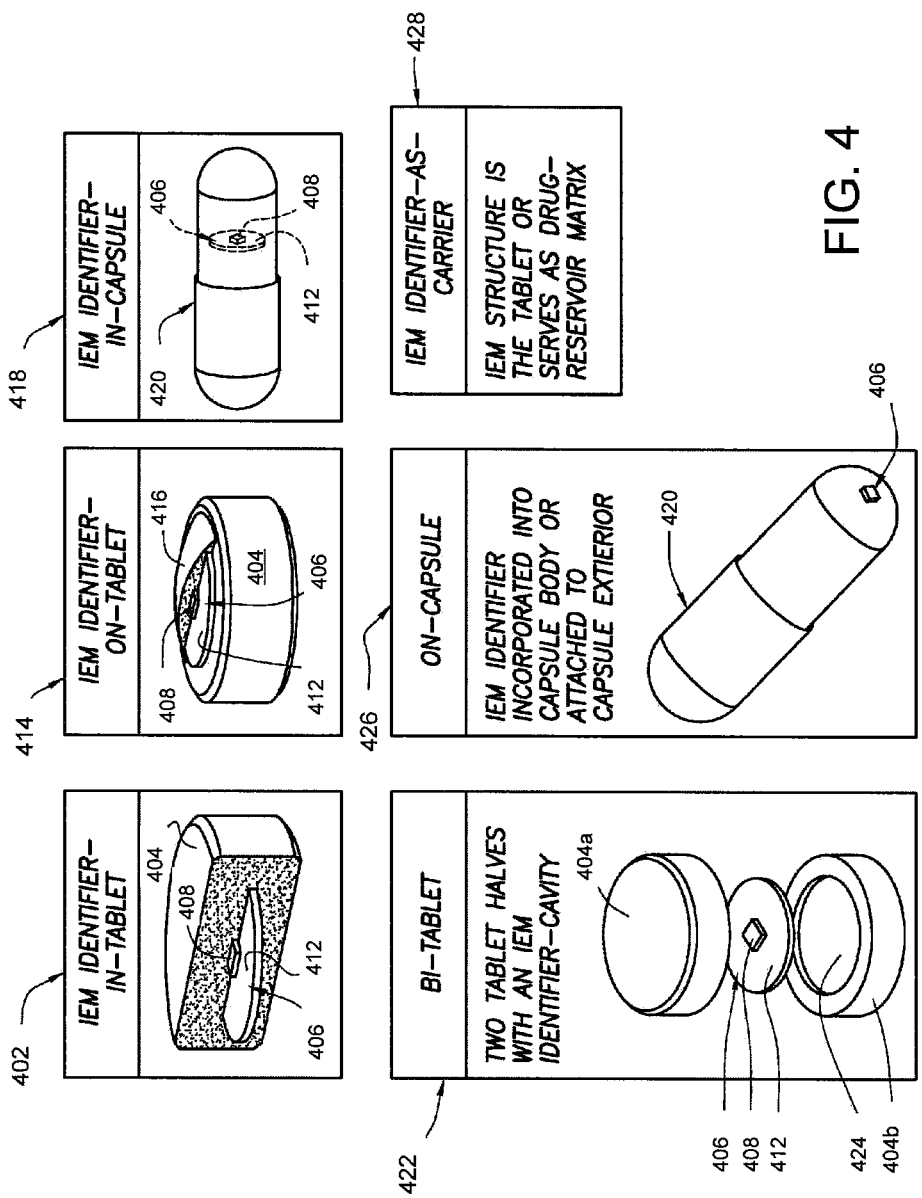
FIG. 4 illustrates views of various IEM configurations.

In one aspect, such manufacturing systems may include an assembly unit configured to stably associate an IEM with an active agent composition (active agent and pharmaceutically acceptable carrier) to produce an IEM device in a variety of configurations, as shown in FIG. 4 (e.g., a drug tablet/pill or a drug-containing capsule). In such an aspect, the IEM may be combined with a composition (e.g., one or more drugs/medications) at the source of manufacture of the composition (e.g., the manufacturer/producer of a pharmaceutical composition) to become a drug-device combination.

In another aspect, such manufacturing systems may include an assembly unit configured to stably associate an IEM with a placebo/non-drug composition to produce a placebo/non-drug IEM device in a variety of configurations, as shown in FIG. 4. The manufacturing system/process may be the same with the exception of replacing the active agent composition with the placebo/non-drug composition (e.g., the IEM is not combined with an active drug/medication at the manufacturer). In such an aspect, the placebo/non-drug IEM device may subsequently be combined with an active agent (e.g. one or more drugs/medications) in a pharmaceutically acceptable carrier/vehicle (e.g., capsule) by a licensed pharmacist (e.g., co-encapsulation).

In view of FIG. 4, for example, in "IEM-in-Tablet" 402, an IEM 406 having a unit 408, e.g., two dissimilar materials and a control device, and a current path extender ("skirt") 412 is present inside of a tablet 404, e.g., by incorporation during tablet pressing or placement in a cavity provided by two tablet halves. Next, in "IEM-On-Tablet" 414, an IEM 406 having a unit 408, e.g., two dissimilar materials and a control device, and a current path extender ("skirt") 412 is communicably associated with a tablet 404. A coating 416, shown in partial form, partially or wholly covers the IEM 406 and may cover at least a portion of the carrier, e.g., tablet 404. Next, in "IEM-In-Capsule" 418, an IEM 406 having a unit 408, e.g., two dissimilar materials and a control device, and a current path extender ("skirt") 412 is communicably associated, e.g., inserted into, a capsule 420. Next, in "Bi-Tablet" 422, an IEM 406 having a unit 408, e.g., two dissimilar materials and a control device, and a current path extender ("skirt") 412 is communicably associated, e.g., disposed within two tablet-halves 404 a and 404 b, respectively in a cavity 424. Next, in "On-Capsule" 426, an IEM 406 having a unit 408 is communicably associated, e.g., attached to an exterior portion of capsule 420. Lastly, in "IEM-As-Carrier" 428, an IEM 406 structure is the tablet or serves as a drug-reservoir matrix.

In one aspect of the present disclosure, such manufacturing systems may include programming devices configured to program/reprogram the circuitry components of the IEM. (e.g., FIG. 3B discussed above—set of address bits 326 fixed when IEM is manufactured). Any convenient programming devices may be employed. In one aspect of the present disclosure the manufacturing system may include a programming unit, wherein the programming unit is configured to confirm that the IEM is functional/operational, and wherein the programming unit is further configured to program the circuitry components (e.g., control logic 202 of the signal generation element 200 in FIG. 2, the readout circuit 316 of the integrated circuit 300 in FIG. 3A-3B, etc.) of the IEM. In such an aspect, the programming unit may program/reprogram the circuitry components of the IEM before, during and/or after it is determined that the IEM is functional/operational. In an alternative aspect, as discussed herein, the circuitry components of the IEM may not be programmable/reprogrammable.

Figure 5:
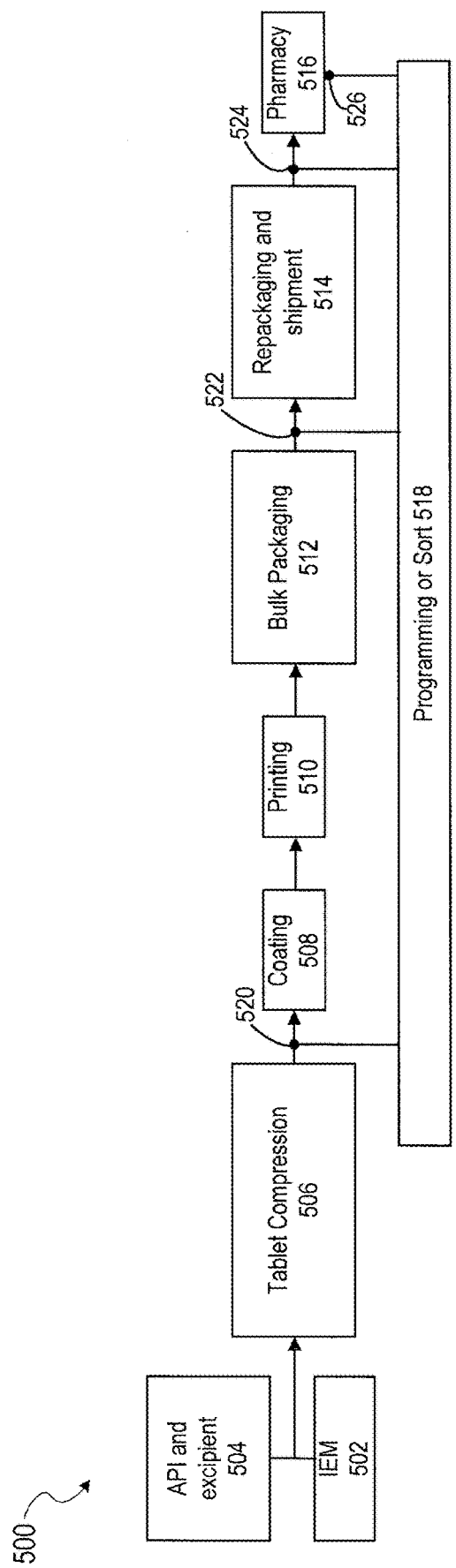
FIG. 5 illustrates a flow diagram of an IEM device lifetime, according to one aspect of the present disclosure.

A process flow diagram 500 of a system configured to program IEMs is shown in FIG. 5. The process 500 begins with an IEM 502 being combined with an active pharmaceutical agent (API) and a physiologically acceptable vehicle 504 into a tablet IEM device 506. Following tablet compression, the resultant tablet may be coated at stage 508 and any printing or labeling applied at stage 510 to produce the final IEM device. Next, the IEM device is sent to a bulk packaging stage 512, where the resultant bulk package of IEM devices is shipped at stage 514 to pharmacy 516 for ultimate sale to a customer. Box 518 illustrates examples of points in the process where information may be transmitted to the IEM and/or information may be received from the IEM. For example, in one aspect of the present disclosure, programming information may be transmitted to the IEM at any of points 520, 522, 524 and 526. Alternatively and/or in addition to transmitting programming information to the IEM at any of points 520, 522, 524 and 526, identifying information (e.g., a unique identifier code) may be retrieved from the IEM at any of these points. In one aspect, such information may be sent to an IEM tracking system database (discussed below).

In an alternative aspect, the tablet IEM device 506 may include a placebo/non-drug IEM device as discussed herein (e.g., the IEM is not combined with an active drug/medication at the manufacturer). Analogous to FIG. 5, the placebo/non-drug IEM device may be coated at stage 508 and any printing or labeling applied at stage 510. Next, the placebo/non-drug IEM device may be sent to a bulk packaging stage 512, where the resultant bulk package of placebo/non-drug IEM devices is shipped at stage 514 to pharmacy 516 for subsequent co-encapsulation by with an active drug/medication by a licensed pharmacist. Analogous to FIG. 5, the IEM of the placebo/non-drug IEM device may or may not be programmable/reprogrammable at points 520, 522, 524, and 526. In various aspects, identifying information (e.g., a unique identification code) may be retrieved from the IEM at any or all of points 520, 522, 524, and 526. In one aspect, such identifying information may be sent to an IEM tracking system database (discussed below).

FIG. 6 illustrates a tracking device 600 usable in a manufacturing, supply chain and/or pharmacy system (e.g., at points 520, 522, 524 and/or 526 in FIG. 5). In FIG. 6, hopper 602 may include a number of IEM devices 604. Here, it should be appreciated that IEM devices 604 may include IEM devices including an active drug/medication or placebo/non-drug IEM devices as discussed herein. Funnel 606 dispenses the IEM devices 604 into a dispenser counter 608. In one aspect of the present disclosure a structure/tube 610 attached to the dispenser counter 608 may include a number of radio frequency (RFID) coils 612 configured to receive/transmit IEM identifier codes of the IEMs of the IEM devices 604 as they pass through the tube 610. In an alternative aspect of the present disclosure, the tube 610 attached to the dispenser counter 608 may include capacitive plates/probes (discussed below) configured to receive/transmit the IEM identifier codes of the IEMs of the IEM devices 604 as they pass through the tube 610. (See FIG. 12A-12B). In general, other capacitive elements shaped in different configurations besides plates may be used according to some embodiments, and embodiments are not so limited. Notably, the tube 610 is appropriately sized to dispense a single IEM device 604 at a time into the container 614 (e.g., bulk packaging container, patient consumer container, etc.) until the container 614 is filled to the desired count of identified IEM devices. In such an aspect, the received (e.g., read) IEM identifier codes may be sent to an IEM tracking system database (discussed below). In further aspects of the present disclosure, the tracking device 600 may include a scanner (not shown, e.g., integrated scanner, attached hand scanner, etc.) configured to scan a container identifier (e.g., See FIG. 7, reference 706 and/or 708) of the container 614. In such an aspect the tracking device 600 and/or a computer system (e.g. manufacturing system, supply chain system, pharmacy system, etc.) in communication therewith is configured to link the container identifier of the container 614 with the received (e.g., read) IEM identifier codes of the IEMs of the IEM devices 604 that passed through the tube 610 into the container 614. In such an aspect, the tracking device 600 and/or the computer system may send such linked information to an IEM tracking system database (discussed below).

Figure 7:
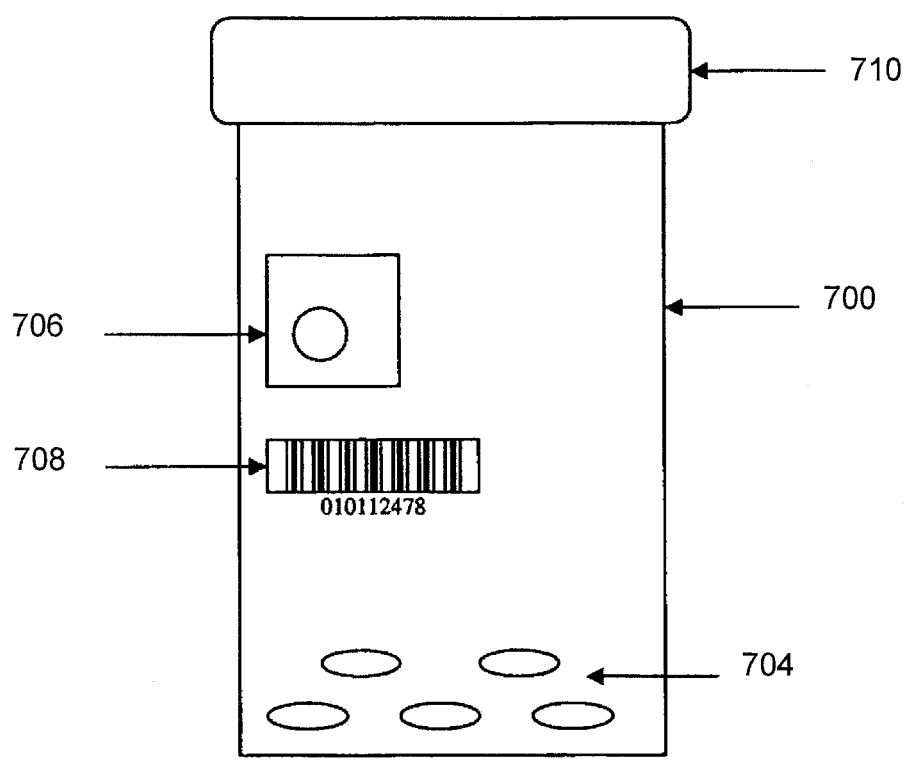
FIG. 7 shows a container that may be produced using the system of FIG. 6, according to one aspect of the present disclosure.

FIG. 7 illustrates a container 700 according to one aspect of the present disclosure. The container 700 may be a bulk packaging container (e.g., filled by a manufacturer) or a consumer patient container (e.g., filled by a pharmacy). The container 700 includes multiple IEM devices 704, identified by a tracking device (e.g., FIG. 6). It should be appreciated that the IEM devices 704 may include IEM devices including an active drug/medication or placebo/non-drug IEM devices as discussed herein. The container 700 further includes a cap 710 and at least one container identifier 706 and/or 708. Similar to FIG. 6, the tracking device may include a scanner configured to scan the at least one container identifier 706 and/or 708 of the container 700. In such an aspect, the tracking device and/or a computer system (e.g. manufacturing system, supply chain system, pharmacy system, etc.) in communication therewith is configured to link the at least one container identifier 706 and/or 708 with the IEM identifier codes of the IEMs of the multiple IEM devices 704 received/read by the tracking device. In such an aspect, the tracking device and/or the computer system may send such linked information to an IEM tracking system database (discussed below).

FIG. 8 illustrates an alternative tracking device 800 in one aspect of the present disclosure. In FIG. 8, a counting board/tray 802 may include integrated capacitive plates/probes 804 positioned at product exit point 806. The integrated capacitive plates/probes 804 are configured to receive/transmit IEM identifier codes of IEMs of IEM devices that pass through product exit point 806. In such an aspect, the counting board/tray 802 may further include circuitry (not shown) configured to receive the IEM identifier codes from the capacitive plates/probes 804 and transmit (e.g., wirelessly) the IEM identifier codes to a computer system (e.g., a pharmacy computer system). Further, in such an aspect, the computer system may be configured to record the transmitted IEM identifier codes. The computer system may be further configured to link (e.g., in a local database) each recorded IEM identifier code with other information including a consumer patient container identifier (e.g., FIGS. 7, 706 and/or 708), a particular drug and dose form (e.g., Furosemide, 20 mg), and/or a particular consumer patient identifier (discussed below). The computer system may be further configured to send such linked information to an IEM tracking system database. In such an aspect, the counting board/tray 802 enables the tracking of IEM devices counted into area 812 and dispensed via product exit point 806 into a consumer patient container. In such a manner, more than one consumer patient may share IEM devices from a single bulk packaging container, but only the IEM devices actually dispensed into a consumer patient's container will be associated with the consumer patient (e.g., a computer system may link the IEM identifier codes of the IEM devices dispensed into the consumer patient's container with a consumer patient identifier). Here, in the context of being dispensed to a consumer patient, it should be appreciated that the IEM devices being tracked may include IEM devices including IEMs combined with an active drug/medication by a manufacturer or IEM devices including placebo/non-drug IEM devices combined with an active drug/medication by a pharmacist (e.g., co-encapsulation) prior to being dispensed.

Further in view of FIG. 8, the counting board/tray 802 may include integrated capacitive plates/probes 808 positioned at product exit point 810. The integrated capacitive plates/probes 808 are configured to receive/transmit IEM identifier codes of IEMs of IEM devices that pass through product exit point 810. In such an aspect, the counting board/tray 802 may further include circuitry (not shown) configured to receive the IEM identifier codes from the capacitive plates/probes 808 and transmit (e.g., wirelessly) the IEM identifier codes to a computer system (e.g., a pharmacy computer system). Further, in such an aspect, the computer system may be configured to confirm/verify IEM devices returned to a bulk packaging container (e.g., not dispensed to a consumer patient). The computer system may be further configured to send such information to an IEM tracking system database. In such an aspect, the counting board/tray 802 enables the tracking of IEM devices poured into area 814 and dispensed via product exit point 810 back into a bulk packaging container. In such a manner, more than one consumer patient may share IEM devices from a single bulk packaging container, while the systems (e.g. computer system, IEM tracking system, etc.) keep track of IEM devices not yet dispensed. Here, it should be appreciated that the IEM devices being tracked may include IEM devices including IEMs combined with an active drug/medication by a manufacturer or IEM devices including placebo/non-drug IEM devices combined with an active drug/medication by a pharmacist (e.g., co-encapsulation) prior to being dispensed.

Pharmacist Co-Encapsulation

As discussed herein, a manufacturer may produce a placebo/non-drug IEM device in a variety of configurations (FIG. 4, e.g., reference 402) by stably associating an IEM with a placebo/non-drug composition. A pharmacy may stock in inventory (e.g., from such a manufacturer) a plurality of bulk packaging containers, wherein each bulk packaging container includes a plurality of placebo/non-drug IEM devices. As discussed herein, each placebo/non-drug IEM device may be hard-coded/programmed with a unique IEM identifier code at the manufacturer level. In further aspects of the present disclosure, each placebo/non-drug IEM device may be hard-coded/programmed with a unique IEM identifier code including a digi-code (e.g., reserved for a particular drug and dose form) at the manufacturer level.

In such an environment, a licensed pharmacist may receive a prescription from a consumer patient. In various aspects of the present disclosure, the prescription may prescribe an IEM-based drug/medication for the consumer patient. A physician of the consumer patient may write such a prescription so that the physician and/or the consumer patient can track (e.g., via an IEM tracking system) whether the consumer patient is taking their prescribed dosages at the prescribed times (e.g., medication adherence).

As indicated, in one aspect of the present disclosure, each placebo/non-drug IEM device of the plurality of placebo/non-drug IEM devices of a bulk packaging container may be hard-coded/programmed with a unique IEM identifier code including a digi-code within a digi-code block reserved for a particular drug and dose form (e.g., Furosemide, 20 mg tablet). In such an aspect, in response to a physician's prescription for an IEM-based drug/medication (e.g., prescription for a total of 60 IEM system trackable Furosemide, 20 mg tablets), a licensed pharmacist may retrieve, e.g., i) a bottle of the prescribed drug/medication (e.g., a 100 count bottle of Furosemide, 20 mg tablets), ii) a bulk packaging container of placebo/non-drug IEM devices hard-coded/programmed with the unique IEM identifier codes including the digi-code within the digi-code block reserved for the prescribed drug and dose form (e.g., a 100 count bulk packaging container of placebo/non-drug IEM devices hard-coded/programmed with unique IEM identifier codes including the digi-code within the digi-code block reserved for Furosemide, 20 mg tablets), and iii) a number of pharmaceutically acceptable carriers/vehicles to fill the prescription (e.g., 60 capsules). The licensed pharmacist may then combine/co-encapsulate the prescribed drug/medication (e.g., a Furosemide, 20 mg tablet) with such a placebo/non-drug IEM device in each pharmaceutically acceptable carrier/vehicle (e.g. capsule) in order to fill the prescription. The licensed pharmacist may then place the combined/co-encapsulated IEM-based drugs/medications onto a tracking device (e.g., FIG. 8, e.g., into area 814 of counting board/tray 802), count the combined/co-encapsulated IEM-based drugs/medications (e.g., FIG. 8, e.g., into area 812) and dispense the combined/co-encapsulated IEM-based drugs/medications (e.g., FIG. 8, e.g., via product exit point 806) into a consumer patient container. As discussed in reference to FIG. 8 above, the tracking device may facilitate the linkage of each unique IEM identifier code (e.g., including the digi-code within the digi-code block reserved for the prescribed drug and dose form) dispensed with other dispensing information (e.g., identifier of the consumer patient container dispensed into, the particular drug and dose form dispensed, identifier of the consumer patient dispensed to, etc.) and the transmission of such linked information to an IEM tracking system database. Notably, in such an aspect, only a bulk packaging container of placebo/non-drug IEM devices hard-coded/programmed with the unique IEM identifier codes including the digi-code within the digi-code block reserved for the prescribed drug and dose form may be utilized to fill the prescription. This may be desired where the tracking of IEM-based drugs/medications is particularly important/sensitive (e.g., Class II drugs).

As indicated, in another aspect of the present disclosure, each placebo/non-drug IEM device of the plurality of placebo/non-drug IEM devices of a bulk packaging container may be hard-coded/programmed with a unique IEM identifier code. In such an aspect, a digi-code block may not have been reserved for a particular drug and dose form (e.g., Furosemide, 20 mg tablet). In such an aspect, in response to a physician's prescription for an IEM-based drug/medication (e.g., prescription for a total of 60 IEM system trackable Furosemide, 20 mg tablets), a licensed pharmacists may retrieve, e.g., i) a bottle of the prescribed drug/medication (e.g., a 100 count bottle of Furosemide, 20 mg tablets), ii) a bulk packaging container of placebo/non-drug IEM devices hard-coded/programmed with the unique IEM identifier codes (e.g., a 100 count bulk packaging container of placebo/non-drug IEM devices hard-coded/programmed with the unique IEM identifier codes), and iii) a number of pharmaceutically acceptable carriers/vehicles to fill the prescription (e.g., 60 capsules). The licensed pharmacist may then combine/co-encapsulate the prescribed drug/medication (e.g., a Furosemide, 20 mg tablet) with such a placebo/non-drug IEM device in each pharmaceutically acceptable carrier/vehicle (e.g. capsule) in order to fill the prescription. The licensed pharmacist may then place the combined/co-encapsulated IEM-based drugs/medications onto a tracking device (e.g., FIG. 8, e.g., into area 814 of counting board/tray 802), count the combined/co-encapsulated IEM-based drugs/medications (e.g., FIG. 8, e.g., into area 812) and dispense the combined/co-encapsulated IEM-based drugs/medications (e.g., FIG. 8, e.g., via product exit point 806) into a consumer patient container. As discussed in reference to FIG. 8 above, the tracking device may facilitate the linkage of each unique IEM identifier code dispensed with other dispensing information (e.g., identifier of the consumer patient container dispensed into, the particular drug and dose for dispensed, identifier of the consumer patient dispensed to, etc.) and the transmission of such linked information to an IEM tracking system database. Notably, in such an aspect, any available bulk packaging container of placebo/non-drug IEM devices hard-coded/programmed with unique IEM identifier codes may be utilized to fill the prescription. This may be desired to reduce pharmacy inventory requirements. In various aspects of the present disclosure, the unique IEM identifier codes of such placebo/non-drug IEM devices may not be linked/associated with a particular drug and dose form until reported by the tracking device to the IEM system tracking database.

IEM System

Various systems may be in data communication with the IEM. Such systems include those discussed in U.S. Patent Application Publication No. 2011/0009715, entitled "Ingestible Event Marker Data Framework", the entire disclosure of which is hereby incorporated by reference herein.

Referring to FIG. 9, an IEM data framework 902 may include IEM data 904, a hub 906, and one or more IEM data systems 908. Here, IEM data 904 includes data associated with an ingestion event, e.g., an act of ingestion. For example, the IEM data 904 may include an identification of an ingested substance (e.g., an IEM identifier code, a digi-code, etc.). The hub 906 includes any hardware, software, and/or communications component(s) in any combination/configuration, which generally function to communicate the IEM data 904. In one aspect, the hub 906 is configured to communicate the IEM data 904 to the IEM data systems 908. For example, the hub 906 may receive the IEM data 904 from an IEM device and forward the IEM data 904, alone or in combination with other data from other sources, to an IEM data system 908. The IEM data systems 908 provide discrete services and/or activities related to the IEM data 904. The discrete services and/or activities include, for example, propagation of information, data, etc., to a particular user, or group of users, via various system component configurations, etc.

In one aspect of the present disclosure, the IEM data 904 may be communicated by an IEM attached to, embedded in, or otherwise integrated with a drug and dose form (e.g., FIG. 4). In another aspect of the present disclosure the IEM may be co-encapsulated with a drug and dose form. Here, the IEM may be configured to communicate the IEM data 904 via various methods (e.g., wireless methods, conductive methods via body tissue and/or fluids, etc.).

In one aspect of the present disclosure, the IEM data 904 may be communicated to, e.g., received by, a receiver. The receiver (e.g., hub, 906) may be embodied in various ways, including an attachable device, an implantable device, a semi-implantable device such as a subcutaneous device, and an externally-applied device such as a personal signal receiver. One example of a personal signal receiver is a "patch" receiver which may be removably affixed to the individual's person, apparel, etc. In one aspect, when such a receiver is affixed or otherwise associated with a consumer patient, programming logic associated with the receiver may be configured to receive the IEM data 904 (e.g., unique IEM identifier code, digi-code, etc.) and communicate the IEM data 904 to a computer-related device, e.g., an IEM data system 908. Various receivers may be in communication with an IEM device. Such receivers include those discussed in U.S. Pat. No. 9,439,599, entitled "Wearable Personal Body Associated Device with Various Physical Configurations", the entire disclosure of which is hereby incorporated by reference herein.

In one aspect of the present disclosure, the hub 906 may include any hardware device, software, and/or communications component(s), as well as systems, subsystems, and combinations of the same which generally function to communicate the IEM data 904, including receiving, storing, manipulating, displaying, processing, and/or transmitting the IEM data 904. Communication of the IEM data 904 to and from the hub 906 includes any transmission means or carriers, and combinations thereof, including wireless, wired, RF, conductive, etc. Here, the hub 906 may include various categories of devices (e.g., personal communication devices, base stations, mobile telephones, etc.).

In one aspect of the present disclosure, the IEM data systems 906 include any hardware component, software component, and/or communications component, as well as networks, systems, and subsystems of the same, which generally function to provide a service, function, activity, etc. related to the IEM data 904 (e.g. IEM identifier code). More specifically, the IEM data systems 908 may include components including a computer, a receiver, a transmitter, an application, a software module, a data storage medium, a relational database, a processor, a memory component, and/or a communication link and the IEM data systems 908 may, for example, collect, manipulate, calculate, transmit, receive, store, and/or otherwise communicate at least a portion of the IEM data 904. Furthermore, the IEM data systems 908 may be integrated with, interoperate with, and/or intercommunicate with one or more commercial systems and may otherwise share or further the IEM data related activities with the one or more commercial systems. Here, commercial systems may include a manufacturer computer system and/or a pharmacy computer system.

In one aspect of the present disclosure, the IEM data systems 908 may include an IEM tracking system. The IEM tracking system may include software and an IEM tracking system database for processing and storing IEM data 904. More specifically, the IEM tracking system may track the life cycle of an IEM from manufacture to shipment, to pharmacy inventory, to delivery to patient, to ingestion by the patient, and to expulsion from the patient. Notably, in such an aspect, the IEM tracking system may be integrated with, interoperate with, intercommunicate with, and otherwise share IEM data 904 (e.g., IEM identifier code data) stored in its IEM tracking system database with one or more commercial systems including manufacturer computer systems and/or pharmacy computer systems in order to monitor consumer patient adherence to a prescribed pharmaceutical therapeutic regimen.

In one aspect of the present disclosure, an IEM tracking system may be in communication with one or more commercial systems including at least one manufacturing system and/or at least one pharmacy system. As discussed herein, such manufacturing systems and/or pharmacy systems may communicate IEM data (e.g., IEM identifier codes, etc.) to the IEM tracking system. In one exemplary aspect, the IEM data may have been recorded by a tracking device (See FIGS. 6 and 8 above) from IEM devices. For example, the IEM tracking system may receive IEM data (e.g., hard-coded/programmed IEM identifier codes read from IEM devices, information linked to hard-coded/programmed IEM identifier codes via the tracking device) from a manufacturer computer system. As another example, the IEM tracking system may receive IEM data (e.g., hard-coded/programmed IEM identifier codes read from IEM devices, information linked to hard-coded/programmed IEM identifier codes via the tracking device) from a pharmacy computer system. In such aspects, the IEM tracking system is configured (e.g., via software, database applications, etc.) to store such IEM data in its IEM tracking system database.

In one exemplary aspect of the present disclosure, an IEM tracking system, storing IEM data compiled from manufacturing systems and/or pharmacy systems, may be queried to identify an unknown IEM identifier code. Here, a plurality of IEM identifier codes may have been relayed (e.g., wirelessly) to a consumer patient computer (e.g., personal computer, mobile phone, etc.) by/from a receiver/patch/hub that has logged the plurality of IEM identifier codes (e.g., from IEMs of IEM devices ingested by the consumer patient). In such an aspect, the consumer patient computer may include a compliance application (e.g., to monitor consumer patient adherence to a prescribed pharmaceutical therapeutic regimen) configured to identify unknown IEM identifier codes. More specifically, the compliance application may be configured to query the IEM tracking system database for expected IEM identifier codes (e.g., IEM identifier codes stored as associated with the drug and dose form being taken by the consumer patient). In such an aspect, the compliance application may be configured to compare these expected IEM identifier codes with the plurality of relayed IEM identifier codes to determine/detect any unknown IEM identifier code. Upon detection, the compliance application may be configured to register the unknown IEM identifier code as an ingestion event pending identification. In such an aspect, the compliance application may be configured to query the IEM tracking system database for a drug and dose form associated with the unknown IEM identifier code. In one aspect, the compliance application may simply receive the identification of the drug and dose form from the IEM tracking system. In another aspect, the compliance application may receive a patient container identifier linked to the unknown IEM identifier code (e.g., uploaded to the IEM tracking system database from a pharmacy computer system that filled the drug and dose form as discussed herein). In such an aspect, the compliance application may be further configured to download all IEM identifier codes associated with that patient container identifier (e.g., that prescription). Such an aspect may be desired when a consumer patient has started taking/tracking a new drug/medication. By proactively downloading all such IEM identifier codes (e.g., associated with the patient container identifier identified based on a detected unknown IEM identifier code) the compliance application can more quickly identify future IEM identifier codes locally without having to again query the IEM tracking system database. In such a way, the compliance application learns the drugs/medications being tracked in the consumer patient. Absent such a feature (e.g., until the compliance application was instructed to expect the new drug/medication), the compliance application would otherwise query the IEM tracking system database each time an IEM identifier code associated with that patient container identifier was detected as an unknown IEM identifier code.

Communication Mode(s)

In one aspect of the present disclosure communication with the IEM of the IEM device occurs via capacitive coupling. Capacitive coupling may be preferred over other modes of communication (e.g., RFID) to ensure data integrity, confidentiality, etc. (e.g., close proximity between capacitive probes/plates and the IEM device may facilitate/promote privacy aspects). Various systems/methods to realize capacitive coupling include those discussed in U.S. Patent Application Publication No. 2012/0220838, entitled "System for Supply Chain Management", the entire disclosure of which is hereby incorporated by reference herein.

Referring to FIG. 10A, a device 1010a (e.g., IEM) inside a pharmaceutical product 1012a, such as a pill or tablet, which is completely packaged up and tested via a probe, is discussed in detail below. In accordance with various aspects of the present disclosure, the device 1010a may be located within the product 1012a or secured to the surface of the product 1012a, as contemplated within the scope of the present disclosure. The device 1010a includes a control module for communication and a memory for storing information, such as an IEM identifier code (See e.g., FIG. 2). The probing of the device 1010a may be performed for multiple purposes (e.g., to ensure that the device 1010a is operational, to read an IEM identifier code programmed within the device 1010a). The probing uses a capacitive coupling approach (e.g., a non-destructive interrogation approach) wherein there is capacitive coupling of a first probing capacitive plate 1020a to a first metal or material 1014a on one side of the device 1010a and a capacitive coupling of a second probing capacitive plate 1030a to a second metal or material 1016a on another side of the device 1010a. Although referred to throughout the present disclosure as capacitive "plates" and/or "probes," it will be understood that any suitable capacitive element may be used to allow for capacitive coupling between components. In one aspect of the present disclosure, the first probing capacitive plate 1020a and the second probing capacitive plate 1030a are associated with a wireless interrogator (e.g. See FIGS. 6 & 8 above). Notably, capacitive plate 1020a is electrically insulated from capacitive plate 1030a (not shown). Various ways to probe using capacitive coupling may be accomplished, e.g., metal, metal pads, etc. In accordance with one aspect of the present disclosure, for example, there is capacitive coupling between material 1014a and capacitive plate 1020a and material 1016a and capacitive plate 1030a. The capacitive plates 1020a and 1030a are probes that can communicate with the device 1010a through capacitive coupling. The capacitive plates 1020a and 1030a are electrically connected to a system (e.g., a manufacturer system, a pharmacy system) that can receive information (e.g., identifier code of the device 1010a) from the capacitive plates 1020a and 1030a as well as process the information (e.g., transmit to the IEM tracking system). Also, in accordance with various aspects of the present disclosure, the pharmaceutical product 1012a may be coated with non-conducting material.

Referring to FIG. 10B, a device 1010b is shown as part of a product 1012b in accordance with one aspect of the present disclosure. The device 1010b includes a first material 1014b and a second material 1016b deposited on the surface of the device 1010b for forming a capacitive connection. The materials 1014b and 1016b are in communication with a control module of the device 1010b. Probes 1020b and 1030b are capacitively coupled to materials 1014b and 1016b, respectively. Thus, as the probes 1020b and 1030b are powered up with an AC voltage (e.g., in the kV range, 50 kHz signal), the materials 1014b and 1016b are capacitively coupled to the probes 1020b and 1030b. Information associated with the device 1010b, that is stored in the memory of the device 1010b (e.g., identifier code of the device 1010b), can be encoded by a control module of the device 1010b and communicated to the probes 1020b and 1030b using capacitive coupling. The external AC signal powers the device 1010b, which then switches its internal antenna in and out of the circuit, modulating the capacitance sensed by the wireless interrogator (e.g., FIGS. 6 & 8) and thereby conveying the information. In such fashion the identifier code and configuration of each device 1010b can be read out at the time of manufacture or subsequently.

Referring to FIG. 10C, a device 1010c is shown secured to a product 1012c in accordance with the present disclosure. The device 1010c includes a first material 1014c and a second material 1016c deposited around the perimeter of a skirt 1018c of the device 1010c with at least a portion of the materials 1014c and 1016c being deposited on the skirt 1018c. Furthermore, the materials 1014c and 1016c are coupled to the control module of the device 1010c to allow for communication through capacitive coupling from the control module of the device 1010c to allow the identity of the device 1010c to be communicated to a system (e.g., manufacturer system, pharmacy system, etc.) through the probes 1020c and 1030c. In accordance with one aspect of the present disclosure, the materials 1014c and 1016c are conductive inks, such as an ingestible graphite or carbon based ink or paste. In such an aspect, the probes 1020c and 1030c are powered by an AC source and when brought close to the materials 1014c and 1016c, the probes 1020c and 1030c can communicate with the device 1010c using capacitive coupling through the materials 1014c and 1016c, respectively. Furthermore, in accordance with another aspect of the present disclosure, probes 1022c and 1032c are positioned proximal to the material 1014c and 1016c at different locations to allow for alternative positioning of the device 1010c or to provide for probing of the device 1010c from an alternative direction. Once the probes 1020c and 1030c are powered with an AC voltage and the device 1010c is located near the probes 1020c and 1030c, then the materials 1014c and 1016c can be used to pass information between the device 1010c and the system (e.g., manufacturer system, pharmacy system, etc.) connected to the probes 1020c and 1030c through capacitive coupling.

Referring to FIG. 10D, a device 1010d is shown in accordance with another aspect of the present disclosure. A conducting material 1014d is deposited on the surface of a material 1019a that is associated with the device 1010d. The material 1019a and the material 1019b of the device 1010d are dissimilar materials and form a partial power source for the device 1010d. For example, the material 1019a may be CuCl and the material 1019b may be Mg. The device 1010d also includes transistors at connection 1019c that are capable of electrically connecting the composite 1014d to V-high or the material 1019b, which is at the same potential as V-low. The device 1010d includes a composite material 1016d that is physically associated with the device 1010d and rests on top of an oxide layer 1017d. The material 1016d may be gold-plated CuCl. Thus, as probes or plates, similar to those discussed in FIGS. 10A-10C are powered by an oscillating or AC voltage source, and are brought close to the device 1010d there is capacitive coupling between the composite 1014d and the composite 1016d and the probes or plates. In accordance with one aspect of the present disclosure, as the voltage source isolates, the energy transferred to the material 1014d and the material 1016d varies accordingly and is stored on the device 1010d. As the voltage source is reduced to zero or quiet, then the device 1010d switches from receiving energy to sending energy to the probes using capacitive coupling. In order to create an oscillating energy source, the transistors 1019c are used to connect and disconnect the material 1014d between the material 1019b (which represents V-low) and V-high. As the material 1014d changes energy levels from V-high to V-low, information (e.g., identifier code of the device 1010d) can be transferred to the probes. Thus, during a portion of the cycle when the power is off or quiet (as shown in FIG. 11C), the device 1010d is able to transfer energy to the probes, which energy includes information about the device 10d. Hence, using capacitive coupling, information may be communicated between the device 1010d and a system (e.g. manufacturer system, pharmacy system, etc.) connected to the probes near the device 1010d.

Referring to FIG. 10E, a co-axial probe with two conductive probes/plates 1020e and 1030e separated by an insulating material 1025e is shown in accordance with another aspect of the present disclosure. The inner conductive probe or plate 1020e is surrounded by the insulating material 1025e, which is surrounded by the outer conductive probe or plate 1030e. The device 1010e is shown as part of a pharmaceutical product 1012e. The device 1010e includes a conducting material or ink 1015e deposited on the side opposite the co-axial probe. As the co-axial probe is positioned close to the product 1012e, the probe 1020e is positioned over the center of the device 1010e and the probe 1030e is positioned above the outer edges of the device

1010e and proximal to the material 1015e. Thus, as described above and with respect to FIG. 11C, as the power source is isolating, energy is transferred from the co-axial probe to the device 1010e and as the power source is shut-off or quiet, then energy is transferred from the device 1010e to the system (e.g., manufacturer system, pharmacy system, etc.) connected to the co-axial probe.

Referring to FIG. 11, a voltage source, e.g., an AC voltage or other isolating or alternating source 1140 may run at a high frequency, e.g., 1 MHz, etc. The voltage source is connected to the probes or plates. The device 1110 may include a control module 1150 and bonding pads 1152 to which the materials (e.g., 1014a and 1016a of FIG. 10A) are coupled. In accordance with one aspect of the present disclosure, inside the device 1110 is a diode 1154, such as a Schottky diode or other type of diode that creates an internal supply voltage, and a switch 1156 with some impedance that is turned on and off which changes the impedance of the device 1110. The variation in the impedance is used to communicate information about the identity of the device 1110 (e.g. IEM identifier code). The change in impedance allows for the information associated with the device 1110 to be encoded and sent to a system (e.g., manufacturer system, pharmacy system, etc.) through the probes using capacity coupling, as represented by the capacitors 1158 and 1160. The information is captured by the system connected to the probes represented by the capacitors and read as Vout through the sampling amplifier across the impedance labeled R-sample.

Once the control module 1150 is brought near or exposed to the voltage source through the plates, there is energy transfer through the capacitive coupling and the device 1110 can produce an oscillation signal, which can be detected. The oscillation signal contains information and the isolating signal can be encoded into, for example, a 1 MHz signal or similar frequency, e.g., 500 KHz, as may be dependent on the degree of capacitive coupling. The voltage of the source 1140 will be determined by how much capacitive coupling is achieved between the capacitive plate or probe (e.g., 1020a and 1030a of FIG. 10A) and the materials (e.g., 1014a and 1016a) thereof. Thus, at a high frequency that represents, perhaps, 5 volts, the capacitive value between the probes and the materials is represented by the capacitors 1158 and 1160.

Referring to FIG. 11A-11B, in accordance with another aspect of the present disclosure, a diode bridge is shown that is a circuit representation of the interaction between the plates (e.g., 1020a and 1030a) and the materials (e.g., 1014a and 1016a) of the device (e.g., 1010a). The isolating voltage present at the plates (labeled "PLATE 1" and "PLATE 2") results in an energy transfer in the form of high voltage and a low voltage for the device (e.g., 1010a). The device (e.g., 1010a) includes a control module as part of the processor or logic unit. The logic unit may be a processor, a microprocessor, a multi-module device or any form of integrated circuit. The logic unit is in communication with the conductive materials (e.g., 1014a and 1016a) and the plates (e.g., 1020a and 1030a, labeled "PLATE 1" and "PLATE 2"). As the plates (e.g., 1020a and 1030a) are powered with an AC source, the logic unit stores energy and later uses that energy to send information.

Referring to FIG. 11C, the power cycle is shown with an active period and a quiet period and the transfer cycle of the device (e.g., 1010a) is shown as the transfer window. In accordance with the present disclosure, the duration of the active period energy is transferred from the power source to the device. Then during the quiet phase, the energy stored by the device is used to transfer energy from the device to the system connected to the probes (e.g., 1020a and 1030a). In this way, information associated with the device can be transferred from the device through the probes to the system connected to the probes. In accordance with various aspects of the present disclosure, the information sent from the device to the system of the probes during the quiet phase is based on the information stored in memory of the device. Thus, even though there is a "1" shown during the transfer window or quiet stage of the power source, the information transferred during the quiet stage or phase of the power source may be a "0".

Referring to FIGS. 12A-12B, in accordance with various aspects of the present disclosure, the capacitive plates/probes and the system connected thereto for receiving information may be integrated or otherwise associated with various structural components and other devices, e.g., a tubular structure 1260 as shown in FIG. 12A having capacitive plates 1220 and 1230. To illustrate, an IEM device 1210 having an IEM may be introduced into the structure 1260. The IEM device 1210 may be introduced manually or automatically via automated means. As the IEM device travels through the structure 1260, the IEM device 1210 is probed by the capacitive plates 1220 and 1230 in the structure 1260. In various aspects, other devices and/or components may be associated. In one example, a database may be associated with the local system (e.g. manufacturer system, supply chain system, pharmacy system, etc.). Such a database may be configured to track each read IEM, wherein the database records data including each read IEM identifier code and the drug and dose form associated with each read IEM. To continue with the foregoing illustration, once all or a portion of the number of IEM devices 1210 (e.g., pills) are probed or "read" via the system associated with the probes/plates 1220 and 1230, the system may communicate, via a transmission unit (e.g., wireless, wired, etc.) read information to an IEM tracking system database for further storage, display, manipulation, etc. In this manner, an individual datum, data, large volumes of data, etc., may be processed for various purposes. One such purpose may be, for example, to track pharmaceuticals in a supply chain application, e.g., during a manufacturing process, during a pharmacy verification process, during a pharmacy prescription process, etc. In one alternative aspect of the present disclosure, using a simple hand held reader (e.g., with an oscillating power source) a user can probe an IEM device (e.g., a pill or tablet including an IEM) and determine an IEM identifier code of the IEM device (e.g., via capacitive coupling). Such an approach may enable the propagation of drug and dose information and control measures across the entire life cycle of the IEM. The life cycle includes, for example, medication manufacture, supply chain management, pharmacy management, and patient use management.

In accordance with various aspects of the present disclosure, there are various components included as part of the device 1010a-1010e. For example, the device 1010a-1010e may be an IEM with a unique identity that can be read using capacitive coupling pre-ingestion and communicated using transconduction post-consumption. Various aspects of an IEM are disclosed in U.S. Pat. No. 7,978,064, entitled "Communication System with Partial Power Source", the entire disclosure of which is hereby incorporated by reference herein. For example, when wetted in the stomach an IEM may activate and convey its unique identifier conductively through body tissues to a compatible receiver (e.g., such as a Band-Aid like adhesive wearable sensor. The receiver may log detected IEMs and also track various physiological parameters (e.g., heart rate, activity). Data are periodically uploaded from the receiver to an external device (e.g., a smartphone or tablet computer). Once on the external device, the uploaded data may be relayed to a cloud-based personal health record, other local applications, a data stores, an IEM tracking system database, etc. depending upon the use case. Various IEM systems operable to use such information are discussed in U.S. Pat. No. 9,119,918, entitled "Probablistic Pharmacokinetic and Pharmacodynamic Modeling", the entire disclosure of which is hereby incorporated by reference herein.

In other aspects of the present disclosure, other modes of communication may supplant or supplement the capacitive coupling approach discussed above. For example, the IEM device may be a multi-mode communication IEM device. Such IEM devices may include those discussed in U.S. Patent Application Publication No. 2009/0256702, the entire disclosure of which is hereby incorporated by reference herein. In such an example aspect, the IEM device may include an ingestible component including a conductive communication module (e.g., communicates conductively via body tissue and/or fluids) and at least one additional non-conductive communication module (e.g., communicates wirelessly via RFID). Similar to above, the IEM device is operable to communicate with various other devices, including transmitters/receivers associated with inventory control, pharmacy control, and inter- and intra-body devices.

Depending on the needs of a particular application, the signal obtained from a particular IEM may be a unique signal (e.g., a signal that uniquely identifies a particular IEM from a plurality of IEMs). In one aspect of the present disclosure, each IEM device of a batch of IEM devices emits a unique signal at least with respect to all of the other IEM devices in the batch (e.g., in a bulk container, in a consumer patient's container). In another aspect, the IEM of each IEM device may emit a universally unique signal (analogous to a human fingerprint). In particular, each signal may provide an IEM identifier code, which may be used to retrieve information about the IEM from an IEM tracking system database. For example, the IEM tracking database of the present disclosure may link each IEM identifier code with a particular pharmaceutical product (e.g., drug and dose form) and a particular consumer patient. In one aspect of the present disclosure the signal may be encrypted in a manner that provides control over access to the signal and the informational content thereof.

Pharmacy Level Mapping

As discussed herein, an IEM may be hard-coded/programmed during its manufacture (e.g., wafer processing). In one aspect of the present disclosure, an IEM can be programmed to operate in a 15-bit mode. In the 15-bit mode, there are $2^{15}$ or 32,768 unique identification codes available for programming (e.g., in a transistor memory, there are only two states, zero or one, so numbers are encoded as binary values). In another aspect of the present disclosure, an IEM may be programmed to operate in a 30-bit mode. In the 30-bit mode, there are $2^{30}$ or 1,073,741,824 unique identification codes available for programming. In yet another aspect of the present disclosure, an IEM may be programmed to operate in a 43-bit mode. In the 43-bit mode, there are $2^{43}$ or 8,796,093,022,208 unique identifier codes available for programming. Here, it should be appreciated that other bit modes (e.g., an x-bit mode with $2x$ unique identification codes available for programming) are contemplated by the present disclosure. Here, in light of high production environments (See U.S. Patent Application Publication No. 2012/0011699, e.g., producing 50,000 or more IEM devices per hour) it should be appreciated that a reuse of unique identification codes may be a practical necessity (e.g., if operating in 15-bit mode).

FIG. 13 illustrates unique IEM identifier codes associated with a 15-bit mode according to one aspect of the present disclosure. For example, during manufacture, IEMs may be hard-coded/programmed with a unique IEM identifier code (e.g., sequentially, randomly, etc.) spanning from fifteen "0's" to fifteen "1's". Similarly, in other aspects, IEMs associated with a 30-bit mode may be hard-coded/programmed with a unique IEM identifier code (e.g., sequentially, randomly, etc.) spanning from thirty "0's" to thirty "1's" and IEMs associated with a 43-bit mode may be hard-coded/programmed with a unique IEM identifier code (e.g., sequentially, randomly, etc.) spanning from forty-three "0's" to forty-three "1's". Here, it should be appreciated that IEMs associated with an x-bit mode may be hard-coded/programmed with a unique IEM identifier code (e.g., sequentially, randomly, etc.) spanning from x "0's" to x "1's".

Pharmacy Level Mapping Without Digi-Code Reservation

In various aspects of the present disclosure (e.g., when a reuse of unique identification codes is not anticipated) IEMs may be hard-coded/programmed, during manufacture, with unique IEM identifier codes determined based on the bit mode (e.g., 30-bit, 43-bit, x-bit, etc.) being utilized. In such an aspect, after hard-coding/programming the IEMs with the unique IEM identifier codes, the IEM manufacturer may transmit (e.g., via a manufacturer system) linkage information (e.g., that associates each hard-coded/programmed unique IEM identifier code to a bulk packaging container identifier) to an IEM tracking system. Further, in such an aspect, each produced IEM may subsequently be used to manufacture, for example, i) an IEM device including an IEM combined with an active drug/medication, or ii) a placebo/non-drug IEM device including an IEM combined with a placebo/non-drug composition. Notably, such manufactured placebo/non-drug IEM devices are not intended to reference a specific drug/medication and thus may not require separate FDA approval as a drug-device combination.

With respect to IEM devices including IEMs combined with an active drug/medication, the IEM device manufacturer may transmit (e.g. utilizing a manufacturer system and/or a tracking device as discussed herein, e.g., FIG. 6) linkage information (e.g., that associates each hard-coded/programmed unique IEM identifier code to a bulk packaging container identifier and/or an identifier of the active drug/medication) to an IEM tracking system. Subsequently, at the pharmacy level, with respect to IEM devices including IEMs combined with an active drug/medication, a pharmacist may (e.g., in response to a consumer patient prescription for an IEM-based drug/medication) simply fill the prescription using the IEM devices including the IEMs combined with the prescribed drug/medication. Further, using a tracking device (e.g., FIG. 6, FIG. 8, etc.) the pharmacy system may generate additional mapping information (e.g., that further associates each hard-coded/programmed unique IEM identifier code to its bulk packaging container identifier and/or to a consumer patient container identifier, and/or to a consumer patient identifier) and send such additional mapping information to the IEM tracking system.

With respect to placebo/non-drug IEM devices including IEMs combined with a placebo/non-drug composition, the IEM device manufacturer may transmit (e.g. utilizing a manufacturer system and/or a tracking device as discussed herein, e.g., FIG. 6) linkage information (e.g., that associates each hard-coded/programmed unique IEM identifier code to a bulk packaging container identifier and/or an identifier of the placebo/non-drug composition) to the IEM tracking system. Subsequently, at the pharmacy level, with respect to placebo/non-drug IEM devices including IEMs combined with a placebo/non-drug composition, a pharmacist may (e.g., in response to a consumer patient prescription for an IEM-based drug/medication) co-encapsulate the placebo/non-drug IEM devices with the prescribed drug/medication in a pharmaceutically acceptable carrier (e.g., capsule). Further, using a tracking device (e.g., FIG. 6, FIG. 8, etc.) the pharmacy system may generate additional mapping information (e.g., that further associates each hard-coded/programmed unique IEM identifier code to an identifier of the active drug/medication prescribed (e.g., drug and dose form) as well as to its bulk packaging container identifier, to a consumer patient container identifier, and/or to a consumer patient identifier) and send the additional mapping information to the IEM tracking system.

Notably, absent such a pharmacy level mapping of the hard-coded/programmed unique IEM identifier codes of the placebo/non-drug IEM devices to an identifier of the active drug/medication prescribed, the IEM tracking system would be unable to associate an active drug/medication with the unique IEM identifier codes of the placebo/non-drug IEM devices. For example, with such a pharmacy level mapping, a receiver/patch/hub associated with a consumer patient may log a unique IEM identifier code associated with a placebo/non-drug IEM device co-encapsulated by a pharmacist with a prescribed medication (e.g., drug "A") and ingested by the consumer patient, the receiver/patch/hub may relay (e.g., wirelessly) the logged unique IEM identifier code to a consumer application of a computer patient computer (e.g., mobile phone), the consumer application may query the IEM tracking system to identify the drug/medication associated with the relayed unique IEM identifier code, the IEM tracking system may lookup the queried unique IEM identifier code in its IEM tracking database to find the pharmacy level mapping of the unique IEM identifier code to the identifier of the active drug/medication prescribed (e.g., drug "A"), the IEM tracking system may then transmit the identifier of the active drug/medication prescribed (e.g., drug "A") to the consumer application, and the consumer application may then confirm/verify consumer patient adherence to the prescribed medication based on the received identifier. In various aspects, when an IEM identifier code is detected through the body of the consumer patient, it can be confirmed that the consumer patient has taken a particular drug and dose form by querying the IEM tracking system database for the particular drug and dose form mapped to the IEM identifier code.

Pharmacy Level Mapping with Digi-Code Reservation

In other aspects of the present disclosure a digi-code block may be reserved (e.g., by an entity in the supply chain, e.g., manufacturer, pharmacy, etc.) for a particular drug and dose form. Here, reserving a digi-code block may be analogized to reserving a block of telephone numbers for a particular geographic region by area code. In this vein, unique IEM identifier codes (e.g., analogous to telephone numbers) including a digi-code (e.g., analogous to an area code) may be reserved for a particular drug and dose form (e.g., Furosemide, 20 mg tablet). FIG. 14 illustrates example digi-code blocks reserved according to this aspect of the present disclosure. In the example, a digi-code block including unique IEM identifier codes including digi-code "100" may be reserved for Furosemide, 20 mg tablets 1402, a digi-code block including unique IEM identifier codes including digi-code "101" may be reserved for Furosemide, 40 mg tablets 1404, and a digi-code block including unique IEM identifier codes including digi-code "111" may be reserved for Furosemide, 80 mg tablets 1406. In the example 15-bit mode of FIG. 14, each reserved digi-code block defines unique IEM identifier codes including a respective three digit digi-code (e.g., "100", "101" and "111") combined with a balance of twelve digits spanning from twelve "0's" to twelve "1's". Digi-code blocks may be similarly reserved in other bit modes (e.g., x-bit, 30-bit, 43 bit, etc.). It should be appreciated that the example digi-codes of FIG. 14 are for purposes of illustration and that a digi-code including any number and/or series of digits, located at any specified position within the IEM identifier codes, is contemplated by the present disclosure.

In various aspects of the present disclosure (e.g., when a reuse of unique identification codes is anticipated) a digi-code block may be reserved. In such an aspect, during the manufacture of IEMs, each IEM may be hard-coded/programmed with a unique IEM identifier code determined based on the bit mode (e.g., x-bit, 15-bit, etc.), wherein each hard-coded/programmed unique IEM identifier code includes the digi-code associated with the reserved digi-code block. In such an aspect, after hard-coding/programming IEMs with unique IEM identifier codes from the reserved digi-code block, the IEM manufacturer may transmit (e.g., via a manufacturer system) linkage information (e.g., that associates each hard-coded/programmed unique IEM identifier code from the reserved digi-code block to a bulk packaging container identifier) to an IEM tracking system. Notably, it may not be desired, at this stage, to associate the produced IEMs with a particular drug and dose form. For example, if the produced IEMs are designated for a particular drug and dose form (e.g., Furosemide, 20 mg), a subsequent IEM device manufacturer could experience supply chain issues (e.g., there may be a limited supply of IEMs, the IEM manufacturer may not produce enough IEMs including unique IEM identifier codes including the digi-code associated with the digi-code block designated for the particular drug and dose form) and/or inventory issues (e.g., IEM device manufacturer may have IEMs in inventory, but may not be able to use them because the hard-coded/programmed unique IEM identifier codes of the IEMs in inventory do not include the digi-code associated with the digi-code block designated for the particular drug and dose form for which the IEM is to be combined, may lead to increased inventory requirements and/or increased supply chain complexity to avoid the risk of not being able to satisfy pharmacy demand). In this vein, each produced IEM may subsequently be used to manufacture, for example, i) an IEM device including an IEM combined with an active drug/medication, or ii) a placebo/non-drug IEM device including an IEM combined with a placebo/non-drug composition. Notably, such manufactured placebo/non-drug IEM devices are not intended to reference a specific drug/medication and thus may not require separate FDA approval as a drug-device combination.

With respect to IEM devices including IEMs combined with an active drug/medication, the IEM device manufacturer may transmit (e.g. utilizing a manufacturer system and/or a tracking device as discussed herein, e.g., FIG. 6) linkage information (e.g., that associates each hard-coded/programmed unique IEM identifier code including the digi-code associated with the reserved digi-code block to a bulk packaging container identifier and/or an identifier of the active drug/medication) to an IEM tracking system. In such an aspect, each hard-coded/programmed unique IEM identifier code including the digi-code associated with the reserved digi-code block now has meaning (e.g., digi-code "101" means "Furosemide 40 mg", etc.). Subsequently, at the pharmacy level, with respect to IEM devices including IEMs combined with an active drug/medication, a pharmacist may (e.g., in response to a consumer patient prescription for an IEM-based drug medication) simply fill the prescription using the IEM devices including the IEMs combined with the active drug/medication prescribed. Further, using a tracking device (e.g., FIG. 6, FIG. 8, etc.) the pharmacy system may generate additional mapping information (e.g., that further associates each hard-coded/programmed unique IEM identifier code including the digi-code associated with the reserved digi-code block to its bulk packaging container and/or to a consumer patient container identifier, and/or to a consumer patient identifier) and send such additional mapping information to the IEM tracking system.

With respect to placebo/non-drug IEM devices including IEMs combined with a placebo/non-drug composition, the IEM device manufacturer may transmit (e.g. utilizing a manufacturer system and/or a tracking device as discussed herein, e.g., FIG. 6) linkage information (e.g., that associates each hard-coded/programmed unique IEM identifier code including the digi-code associated with the reserved digi-code block to a bulk packaging container identifier and/or an identifier of the placebo/non-drug composition) to the IEM tracking system. Notably, with respect to the placebo/non-drug IEM devices, it may not be desired, at this stage, to associate the produced placebo/non-drug IEM devices with a particular drug and dose form. For example, if the produced placebo/non-drug IEM devices are designated for a particular drug and dose form (e.g., Furosemide, 20 mg), a pharmacy could experience supply chain issues (e.g., there may be a limited supply of placebo/non-drug IEM devices, the IEM device manufacturer may not produce enough placebo/non-drug IEM devices including unique IEM identifier codes including the digi-code associated with the digi-code block designated for the particular drug and dose form to be filled) and/or inventory issues (e.g., the pharmacy may have placebo/non-drug IEM devices in inventory, but may not be able to use them because the hard-coded/programmed unique IEM identifier codes of the placebo/non-drug IEM devices in inventory do not include the digi-code associated with the digi-code block designated for the particular drug and dose form to be filled, may lead to increased inventory requirements and/or increased supply chain complexity to avoid the risk of not being able to satisfy consumer patient demand). Subsequently, at the pharmacy level, with respect to placebo/non-drug IEM devices including IEMs combined with a placebo/non-drug composition, a pharmacist may (e.g., in response to a consumer patient prescription for an IEM-based drug medication) co-encapsulate the placebo/non-drug IEM devices with the prescribed drug/medication in a pharmaceutically acceptable carrier (e.g., capsule). Here, such co-encapsulation is generally held as a form of compounding. Further, using a tracking device (e.g., FIG. 6, FIG. 8, etc.) the pharmacy system may generate additional mapping information (e.g., that further associates each hard-coded/programmed unique IEM identifier code including the digi-code associated with the reserved digi-code block to an identifier of the active drug/medication prescribed (e.g., drug and dose form) as well as to its bulk packaging container identifier, to a consumer patient container identifier, and/or to a consumer patient identifier) and send the additional mapping information to the IEM tracking system. In such an aspect, each hard-coded/programmed unique IEM identifier code including the digi-code associated with the reserved digi-code block now has meaning (e.g., digi-code "101" means "Furosemide 40 mg", etc.).

Notably, absent such a pharmacy level mapping of the hard-coded/programmed unique IEM identifier code including the digi-code associated with the reserved digi-code block of the placebo/non-drug IEM device to an identifier of the active drug/medication prescribed, the IEM tracking system would be unable to associate an active drug/medication with the unique IEM identifier code including the digi-code associated with the reserved digi-code block of the placebo/non-drug IEM device. For example, with such a pharmacy level mapping, a receiver/patch/hub associated with a consumer patient may log a unique IEM identifier code including a digi-code associated with a reserved digi-code block associated with a placebo/non-drug IEM device co-encapsulated by a pharmacist with a prescribed medication (e.g., drug "B") and ingested by the consumer patient, the receiver/patch/hub may relay (e.g., wirelessly) the logged unique IEM identifier code including the digi-code associated with the reserved digi-code block to a consumer application of a computer patient computer (e.g., mobile phone), the consumer application may query the IEM tracking system to identify the drug/medication associated with the relayed unique IEM identifier code including the digi-code associated with the reserved digi-code block, the IEM tracking system may lookup the queried unique IEM identifier code including the digi-code associated with the reserved digi-code block in its IEM tracking database to find the pharmacy level mapping of the unique IEM identifier code including the digi-code associated with the reserved digi-code block to the identifier of the prescribed medication (e.g., drug "B"), the IEM tracking system may then transmit the identifier of the active drug/medication prescribed (e.g., drug "B") to the consumer application, and the consumer application may then confirm/verify consumer patient adherence to the prescribed medication based on the received identifier. In various aspects, when an IEM identifier code including a digi-code associated with a reserved digi-code block is detected through the body of the consumer patient, it can be confirmed that the consumer patient has taken a particular drug and dose form by querying the IEM tracking system database for the particular drug and dose form mapped to the IEM identifier code including the digi-code associated with the reserved digi-code block.

Pharmacy Level Mapping with IEM Reprogramming

In an alternative aspect of the present disclosure, the IEM of an IEM device may be programmable/reprogrammable. More specifically, in line with FIG. 5, the IEM of an IEM device may be programmed/reprogrammed at the pharmacy level (e.g., reference 526). A programmable/reprogrammable IEM may be desired under circumstances wherein fraud on or tricking of the IEM tracking system (e.g., discussed herein) is not of concern. In such an aspect, during manufacture, each IEM may either not be programmed with an IEM identifier code or may be programmed with a generic/non-specific IEM identifier code. Similar to other aspects of the present disclosure, each produced IEM may subsequently be used to manufacture, for example, i) an IEM device including an IEM combined with an active drug/medication, or ii) a placebo/non-drug IEM device including an IEM combined with a placebo/non-drug composition. Notably, such manufactured placebo/non-drug IEM devices are not intended to reference a specific drug/medication and thus may not require separate FDA approval as a drug-device combination.

At the pharmacy level, with respect to IEM devices including IEMs combined with an active drug/medication, a pharmacist may (e.g., in response to a consumer patient prescription for an IEM-based drug/medication) simply fill the prescription using the IEM devices including the IEMs combined with the prescribed drug/medication. Here, the pharmacy system (e.g., tracking device of FIG. 6., FIG. 8, etc.) may be further configured to program/reprogram each IEM of each IEM device as it is counted (e.g., as it passes through tube 610 or product exit point 806, etc.). In one aspect of the present disclosure, the IEMs may be programmed/reprogrammed using unique IEM identifier codes including a digi-code associated with a digi-code block reserved for the prescribed drug/medication. Here, the reserved digi-code block may be recognized in the field (e.g., same as manufacturer, See e.g., FIGS. 15, 1504 and 1506, i.e., digi-code "100" reserved for Furosemide, 20 mg tablets). In another aspect of the present disclosure, the IEMs may be programmed/reprogrammed using any subset of possible unique IEM identifier codes. (e.g., See, e.g., FIG. 15, 1508 versus 1510, e.g., digi-code "101" reserved for Furosemide, 40 mg tablets at the manufacturer level, versus digi-code "110" reserved for Furosemide, 40 mg tablets at the pharmacy level). In yet another aspect, the IEMs may be programmed/reprogrammed using a generic/arbitrary subset of unique IEM identifier codes. In such an aspect, only a small number of unique IEM identifier codes is required (e.g., the count of the IEM-based drug/medication prescribed). Further, using the tracking device (e.g., FIG. 6, FIG. 8, etc.) the pharmacy system may generate mapping information (e.g., that associates each programmed/reprogrammed unique IEM identifier code to an identifier of the active drug/medication prescribed (e.g., drug and dose form) as well as to a bulk packaging container identifier, to a consumer patient container identifier, and/or to a consumer patient identifier) and send such mapping information to the IEM tracking system. In such an aspect, each programmed/reprogrammed unique IEM identifier code (e.g., with or without a digi-code) now has meaning (e.g., digi-code "101" means "Furosemide 40 mg", etc.).

At the pharmacy level, with respect to placebo/non-drug IEM devices including IEMs combined with a placebo/non-drug composition, a pharmacist may (e.g., in response to a consumer patient prescription for an IEM-based drug/medication) co-encapsulate the placebo/non-drug IEM devices with the prescribed drug/medication in a pharmaceutically acceptable carrier (e.g., capsule). Here, such co-encapsulation is generally held as a form of compounding. Here, similar to above, the pharmacy system (e.g., tracking device of FIG. 6., FIG. 8, etc.) may be further configured to program/reprogram each IEM of each IEM device as it is counted (e.g., as it passes through tube 610 or product exit point 806, etc.). Further, using the tracking device (e.g., FIG. 6, FIG. 8, etc.) the pharmacy system may generate mapping information (e.g., that associates each programmed/reprogrammed unique IEM identifier code to an identifier of the active drug/medication prescribed (e.g., drug and dose form) as well as to a bulk packaging container identifier, to a consumer patient container identifier, and/or to a consume patient identifier) and send the mapping information to the IEM tracking system. Similar to above, each programmed/reprogrammed unique IEM identifier code (e.g., with or without a digi-code) now has meaning (e.g., digi-code "101" means "Furosemide 40 mg", etc.).

Notably, absent such a pharmacy level mapping of the programmed/reprogrammed unique IEM identifier codes of such IEM devices to an identifier of the prescribed drug/medication, the IEM tracking system would be unable to associate an active drug/medication with the unique IEM identifier codes of the IEM devices. For example, with such a pharmacy level mapping, a receiver/patch/hub associated with a consumer patient may log a unique IEM identifier code associated with an IEM device ingested by the consumer patient, the receiver/patch/hub may relay (e.g., wirelessly) the logged unique IEM identifier code to a consumer application of a computer patient computer (e.g., mobile phone), the consumer application may query the IEM tracking system to identify the drug/medication associated with the relayed unique IEM identifier code, the IEM tracking system may lookup the queried unique IEM identifier code in its IEM tracking database to find the pharmacy level mapping of the unique IEM identifier code to the identifier of the prescribed medication (e.g., drug "C"), the IEM tracking system may then transmit the identifier of the prescribed medication (e.g., drug "C") to the consumer application, and the consumer application may then confirm/verify consumer patient adherence to the prescribed medication based on the received identifier. In various aspects, when an IEM identifier code is detected through the body of the consumer patient, it can be confirmed that the consumer patient has taken a particular drug and dose form by querying the IEM tracking system database for the particular drug and dose form mapped to the IEM identifier code.

Pharmacy Dispensing of IEM Devices

Referring to FIG. 16, an example flow diagram for dispensing IEM devices at the pharmacy level, according to one aspect of the present disclosure, is presented. When dispensing/filling a prescription for an IEM-based drug/medication 1602, it may be first be determined whether a bulk package of IEM devices is available 1604. If not available, a bulk package of IEM devices may be ordered (e.g., from a manufacturer/supplier, automatically via the pharmacy system, etc.) 1606. If available, it may determined 1608 whether the bulk package includes i) IEM devices including IEMs combined with an active drug/medication, or ii) placebo/non-drug IEM devices including IEMs combined with a placebo/non-drug composition.

In a first aspect of FIG. 16, if the bulk package includes IEM devices including IEMs (e.g., with or without digi-codes) combined with an active drug/medication 1610 an identifier of the bulk package (e.g., FIGS. 7, 706 and/or 708, FIG. 15, 1516) may be scanned/manually entered 1612. For example, a pharmacist may scan/manually enter the identifier of the bulk package into its pharmacy computer system. This may be accomplished, for example, using a scan tool, a keyboard, a mobile application, a web-browser and/or other software (e.g., a dispenser application). Next, it may optionally be determined whether the entered bulk packaging identifier has been linked to a particular active drug (e.g., Furosemide, 20 mg). This may be determined, for example, by querying the IEM tracking system database. As discussed herein, an IEM device manufacturer may have transmitted this information (e.g., linking the bulk package identifier to a particular active drug) to the IEM tracking system. Next, a tracking device (e.g., FIG. 8) may be used to count the IEM devices (e.g., and read their respective IEMs) 1614 into a consumer patient container. Next, software (e.g., a dispenser application) may be used to map the IEMs of the counted IEM devices (e.g., FIG. 15, 1518) to the scanned bulk package identifier (e.g., FIG. 15, 1516), a consumer patient container identifier (e.g., FIG. 15, 1520, e.g., scanned via a scan tool, manually entered, etc.), and/or a consumer patient identifier (e.g., FIG. 15, 1522), e.g., manually entered, previously stored in the dispenser application, etc.) in the pharmacy system 1616. The prescription may then be dispensed to the consumer patient and the pharmacy level mapping (FIG. 15, 1512) may be uploaded/transmitted by the pharmacy system to the IEM tracking system for storage in its IEM tracking database 1618.

In a second aspect of FIG. 16, if the bulk package includes placebo/non-drug IEM devices including IEMs (e.g., with our without digi-codes) combined with a placebo/non-drug composition 1620 an identifier of the bulk package (e.g., FIGS. 7, 706 and/or 708, FIG. 15, 1516) may be scanned/manually entered 1622. For example, a pharmacist may scan/manually enter the identifier of the bulk package into its pharmacy computer system. This may be accomplished, for example, using a scan tool, a keyboard, a mobile application, a web-browser and/or other software (e.g., a dispenser application). Next, it may be determined (e.g., by querying the IEM tracking system database) whether the entered bulk packaging identifier has been previously mapped 1624 to a particular active drug/medication (e.g., Furosemide, 20 mg). With respect to placebo/non-drug IEM devices, this may have occurred when the pharmacy system filled another prescription for an IEM-based drug medication. If so, it may be determined whether the active drug associated with the entered bulk packaging identifier is the same active drug/medication currently being filled 1626. If they are not the same active drug/medication, the pharmacist must choose another available bulk package 1628 and start the process again 1604. If they are the same active drug/medication or the entered bulk packaging identifier was not previously mapped to a particular active drug/medication 1624, the licensed pharmacist may co-encapsulate the placebo/non-drug IEM devices from the bulk package with the prescribed drug/medication in a pharmaceutically acceptable carrier (e.g., capsule) 1630. Next, a tracking device (e.g., FIG. 8) may be used to count the IEM devices (e.g., and read their respective IEMs) 1632 into a consumer patient container. Next, software (e.g., a dispenser application) may be used to map the IEMs of the counted IEM devices (e.g., FIG. 15, 1518) to the active drug/medication prescribed, the scanned bulk package identifier (e.g., FIG. 15, 1516), a consumer patient container identifier (e.g., FIG. 15, 1520, e.g., scanned via a scan tool, manually entered, etc.), and/or a consumer patient identifier (e.g., FIG. 15, 1522), e.g., manually entered, previously stored in the dispenser application, etc.) in the pharmacy system 1634. The prescription may then be dispensed to the consumer patient and the pharmacy level mapping (FIG. 15, 1512) may be uploaded/transmitted by the pharmacy system to the IEM tracking system for storage in its IEM tracking database 1618. Furthermore, the pharmacy system may upload/transmit additional information (e.g., FIG. 8, IEMs of IEM devices that pass through product exit point 810 back to the bulk package, etc.) to the IEM tracking system 1636. In one aspect of the present disclosure, any remaining placebo/non-drug IEM devices mapped to the bulk package identifier will be used to fill a prescription(s) for the same associated active drug/medication.

Under this second aspect, each bulk package can be mapped/assigned, at the pharmacy level, at the time needed. Here, it should be appreciated that multiple bulk packages may be processed in such a manner and that a pool of placebo/non-drug IEM devices from multiple bulk packages may be assigned and combined to fill a consumer patient's prescription for an IEM-based drug/medication (See e.g., FIG. 15, 1516, i.e., pool of IEM devices from "Pkg 113" and "Pkg 114", both linked to Furosemide, 20 mg tablet are combinable to fill a consumer patient's prescription). Furthermore, it should be appreciated that more than one consumer patient may share IEM devices from a single bulk package, but each consumer patient will receive a subset of unique IEM identifier codes from the single bulk package.

Here, in light of FIG. 16, it should be appreciated that a prescription for an IEM-based drug/medication may be filled from both IEM devices including IEMs combined with an active drug/medication 1610 and placebo/non-drug IEM devices including IEMs combined with a placebo/non-drug composition 1620 co-encapsulated with the active drug/medication by a licensed pharmacist. In either case, when an IEM identifier code is conductively detected through the consumer patient, it can be confirmed that the consumer patient has taken a particular drug and dose form by querying the IEM tracking database for the particular drug and dose form linked to the IEM identifier code. In such an aspect, further associated information (e.g., consumer patient identifier, consumer patient container identifier, and/or bulk packaging identifier, etc.) may be used to confirm that a particular consumer patient has taken a particular drug and dose form.

In an alternative aspect of the present disclosure, it may be determined that the bulk package includes i) IEM devices including programmable/reprogrammable IEMs combined with an active drug/medication, or ii) placebo/non-drug IEM devices including programmable/reprogrammable IEMs combined with a placebo/non-drug composition. Here, further to the processes described above, the pharmacist may program each programmable/reprogrammable IEM with a unique IEM identifier code as discussed above (e.g., from a digi-code block, a subset of arbitrary identifier codes, etc.).

Conventionally, when a licensed pharmacist is dispensing a prescribed drug and dose form, prescription processing software is already being utilized for various reasons (e.g., to process third party insurance claims on behalf of the consumer patient, to check for possible drug interactions, to check for possible allergies, to document the prescribed medication, etc.). In one aspect of the present disclosure, the above-described functionality may be integrated seamlessly with such prescription processing software. In another aspect of the present disclosure, the above described functionality may be a stand-alone dispensing application. In yet another aspect of the present disclosure the above described functionality may be partially integrated with such prescription processing software and partially integrated with such a dispensing application.

43-Bit Mode Example

In one aspect of the present disclosure, an IEM may be programmed to operate in a 43-bit mode. In line with above, in the 43-bit mode, there are $2^{43}$ or 8,796,093,022,208 unique identifier codes available for programming. As such, the reservation of digi-code blocks, discussed herein, may be practically unnecessary. However, there remains the need to associate other specific information with the active drug/medication of interest. Here, in line with the section "Pharmacy Level Mapping Without Digi-Code Reservation" above, the IEM manufacturer and/or the IEM device manufacturer (e.g., may be the same or a different manufacturing entity) may transmit linkage information (e.g., that associates each hard-coded/programmed unique IEM identifier code to further identifying information discussed above) to an IEM tracking system. Further, the pharmacy system may transmit additional mapping information (e.g., that associated each hard-coded/programmed unique IEM identifier code to additional identifying information discussed above) to the IEM tracking system. Subsequently, a consumer application of a consumer patient computer may utilize such information (e.g., stored in the IEM tracking system database) to identify an active drug/medication associated with a unique IEM identifier code detected/logged by a receiver/patch/hub of a consumer patient after ingestion of an IEM device (e.g., versions discussed herein). More specifically, the consumer application can confirm/verify, based on the identity of the active drug/medication retrieved from the IEM tracking system database, whether the consumer patient has adhered to their prescribed medication.

Further in such an aspect, and similar to previous discussions herein, it may be desirable to use the wireless interrogator during manufacture to record the unique IEM identifier code (e.g., contained with MIT or drug tablet) and store in the IEM tracking system database (e.g., associating each group of IEM identifier codes with the corresponding bulk packaging identifier). At the time of dispensing, a pharmacist can scan the bulk packaging identifier (or enter such code manually) using a mobile application, web-browser, or other software. At this time, if the bulk packaging identifier is not already assigned, it can be designated to map to a particular drug and dose form (e.g., Furosemide 20 mg). At this point, remaining IEM devices within that particular bulk package will be reserved for future prescriptions using the same designated drug and dose form. In this manner, a pharmacist can have a pool of IEM devices in separate bulk packages (e.g., bottles), where each bulk package is assignable at the time needed to any drug. Subsequently, when a patient-facing application first detects an unknown IEM identifier code uploaded from a wearable sensor, it can register this as an unknown ingestion event pending identification. When possible, a query from the computer or smartphone can check the IEM identifier code against the back-end database (IEM system tracking database). The query will report the corresponding bulk packaging identifier and cause the patient's device to download all IEM identifier codes associated with that bulk package. This enables quick local identification of all future IEM devices that may be associated with the prescription. More than one consumer patient may share IEM devices from a single bottle, but each consumer patient's IEM identifier codes will be a unique subset of the IEM identifier codes contained within the bulk package assigned by the pharmacist to the particular drug dose form. There are other ways of uniquely associating IDs with a particular prescription and consumer patient. For instance, the wireless interrogator may be miniaturized, enabling each unique IEM identifier code to be identified as it passes from the pharmacist's counting board through an electronic funnel and into the consumer patient's pill bottle. This method would individually associate each IEM identifier code with a particular drug dose form and patient identifier at the server database level, obviating the need for tracking a bulk packaging identifier.

15-Bit Mode Example

In another aspect of the present disclosure, an IEM may be programmed to operate in a 15-bit mode. In line with above, in the 15-bit mode, there are $2^{15}$ or 32,768 unique identifier codes available for programming. In such an aspect, it should be appreciated that a reuse of unique identifier codes may be required. As such, the reservation of digi-code blocks, discussed herein, may be practical. Here, in line with the section "Pharmacy Level Mapping With Digi-Code Reservation" above, the IEM manufacturer and/or the IEM device manufacturer (e.g., may be the same or a different manufacturing entity) may transmit linkage information (e.g., that associates each hard-coded/programmed unique IEM identifier code including a digi-code associated with a reserved digi-code block to further identifying information discussed above) to an IEM tracking system. Further, the pharmacy system may transmit additional mapping information (e.g., that associates each hard-coded/programmed unique IEM identifier code including the digi-code associated with the reserved digi-code block to additional identifying information discussed above) to the IEM tracking system. Subsequently, a consumer application of a consumer patient computer may utilize such information (e.g., stored in the IEM tracking system database) to identify an active drug/medication associated with a unique IEM identifier code including the digi-code associated with the reserved digi-code block detected/logged by a receiver/patch/hub of a consumer patient after ingestion of an IEM device (e.g., versions discussed herein). More specifically, the consumer application may query the IEM tracking system database (e.g., via a Boolean "AND") for the particular drug and dose form mapped to the IEM identifier code including the digi-code associated with the reserved digi-code block AND a unique consumer patient identifier (e.g., consumer patient mobile phone number, patient MAC address, IMEA, etc.). Such an approach dramatically reduces the number of unique digi-code blocks needed within the 15-bit mode. Instead of reserving a digi-code block for each possible drug and dose form, a unique digi-code block is only needed for each of the number of drug and dose forms being tracked for the consumer patient simultaneously (e.g., 5 or 6 digi-code blocks reserved at the patient level). In one aspect, for example, a hypothetical digi-code of "A-10" could map to Furosemide 20 mg for one consumer patient and to Ibuprofen 200 mg for another consumer patient. It should be appreciated that such an approach is also applicable to other bit modes (e.g., x-bit mode). Under such an approach, the consumer application can confirm/verify, based on the identifier of the active drug/medication retrieved from the IEM tracking system database, whether the consumer patient has adhered to their prescribed medication.

Further in such an aspect, and similar to above, a challenging use case is one in which limited unique IDs are available. One solution is to perform a Boolean AND of a digi-code and some form of consumer patient unique identifier so that a particular digi-code maps to a particular active drug/medication only if used by a particular consumer patient at any time. This approach dramatically reduces the total need for unique digi-code blocks. Instead of a digi-code for each drug and dose form (e.g., type and strength), we now only need unique digi-codes sufficient for the total number of medications (and dose strengths) a consumer patient is tracking simultaneously. According to this process (e.g., which also can work equally well for 43b and other high-address space modes), a pharmacist would assign a digi-code by consumer patient-specific identifier (e.g., mobile phone number, MAC Address, IMEA) AND the medication of interest (e.g., Furosemide 20 mg). The downloaded drug map to the consumer patient's mobile device would be specific for that consumer patient alone. Therefore, a hypothetical digi-code of "A-10" could map to Furosemide 20 mg for one consumer patient and Ibuprofen 200 mg for another consumer patient. According to this aspect, there would still be a need for more than one manufactured product (MITs segregated by digi-code), but the total number of such digi-code SKUs would be reduced, potentially dramatically. Further, in such an aspect, the pharmacist would have to know and enter unique consumer patient-facing identification information. However, the use of ubiquitous mobile phone numbers would entail a minor change in flow. Finally, in such an aspect, any active drug/medication of interest could be assigned to any digi-code by the pharmacist. This greatly simplifies the process of expanding the number of available "digital drugs" (i.e., active drugs/medications capable of adherence tracking by ingestion of an associated IEM device).

While various details have been set forth in the foregoing description, it will be appreciated that the various aspects of the techniques may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices (e.g. floppy disk, hard disk drive, Compact Disc (CD), Digital Video Disk (DVD), or digital tape). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components, and/or electrically interacting components, and/or electrically interactable components, and/or optically interacting components, and/or optically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A system to track consumer patient adherence to a drug and dose form, the system comprising:
  a tracking device comprising at least one capacitive element and a structure to position an Ingestible Event Marker (IEM) device in proximity to the at least one capacitive element, the tracking device configured to:
    process a plurality of IEM devices, wherein each IEM device includes a pharmaceutical composition dispensed by a pharmacy according to a prescription received from a consumer patient that is co-encapsulated at the pharmacy with an IEM capable of storing an IEM identifier code and including no identifying information tied to the pharmaceutical composition or the prescription prior to the co-encapsulation,
    program each of the plurality of IEM devices with a unique IEM identifier code that disambiguates each IEM device among the plurality of IEM devices, using the capacitive element; and
    interrogate each IEM, via capacitive coupling, as each IEM device passes through the structure;
  a database configured to record the unique IEM identifier code to its respective IEM and link each received IEM identifier code to additional information, the additional information including at least one of its respective pharmaceutical product co-encapsulated with the IEM or the prescription of the consumer patient; and
  a computer system communicatively coupled to the tracking device and configured to:
    receive each unique IEM identifier code read from each interrogated IEM; and
    store each unique IEM identifier code with at least one of its respective pharmaceutical product co-encapsulated with the IEM or the prescription, into the database.

2. The system of claim 1, wherein the computer system further comprises a transmission unit configured to transmit each received IEM identifier code and the additional information linked to each received IEM identifier code to an IEM tracking system for storage in an IEM tracking system database.

3. The system of claim 1, wherein the computer system is a pharmacy computer system, wherein the tracking device is a counting board, and wherein the at least one capacitive element is positioned where each IEM device exits the counting board after being counted.

4. The system of claim 1, wherein the structure comprises a cylindrical portion, and wherein the at least one capacitive element is positioned within the cylindrical portion.

5. The system of claim 1, wherein each IEM comprises a first material and a second material, and wherein the at least one capacitive element comprises a first capacitive plate configured to capacitively couple the first material of each IEM and a second capacitive plate configured to capacitively couple the second material of each IEM.

6. The system of claim 1, wherein each IEM is stably associated with either a drug composition or a non-drug composition.

7. The system of claim 1, wherein the computer system is an IEM device manufacturer computer system, wherein each IEM is stably associated with a drug composition, and wherein the database is configured to link each received IEM identifier code to an active drug identifier.

8. The system of claim 1, wherein the computer system is a pharmacy computer system, wherein each IEM is stably associated with a non-drug composition co-encapsulated with an active drug, and wherein the database is configured to link each received IEM identifier code to an identifier of the active drug.

9. The system of claim 8, wherein each IEM has been coded with a unique IEM identifier code by a manufacturer that can be reprogrammed at a pharmacy.

10. The system of claim 8, wherein each IEM has been hard-coded with a unique IEM identifier code comprising a digi-code associated with a reserved digi-code block by a manufacturer.

11. The system of claim 1, wherein each IEM is programmed to operate in one of a 15-bit mode, a 30-bit mode, or a 43-bit mode.

12. The system of claim 1, wherein the additional information further comprises at least one of a particular drug and dose form, a consumer patient container identifier, or a consumer patient identifier.

13. The system of claim 1, further comprising a scanner configured to scan at least one of a bulk packaging identifier or a consumer patient container identifier, wherein the database is further configured to link each received IEM identifier code to the at least one of the bulk packaging identifier or the consumer patient container identifier.

14. A system to track consumer patient adherence to a drug and dose form, the system comprising:

a pharmacy system, comprising:
    a tracking device comprising at least one capacitive element and a structure to position an Ingestible Event Marker (IEM) device in proximity to the at least one capacitive element, the tracking device configured to:
        process a plurality of IEM devices, wherein each IEM device includes a pharmaceutical composition dispensed by a pharmacy according to a prescription received from a consumer patient that is co-encapsulated at the pharmacy with an IEM capable of storing an IEM identifier code and including no identifying information tied to the pharmaceutical composition or the prescription prior to the co-encapsulation,
        program each of the plurality of IEM devices with a unique IEM identifier code that disambiguates each IEM device among the plurality of IEM devices, using the capacitive element; and
        interrogate each IEM, via capacitive coupling, as each IEM device passes through the structure;
    a database configured to record the unique IEM identifier code to its respective IEM and link each received IEM identifier code to additional information, the additional information including at least one of its respective pharmaceutical product co-encapsulated with the IEM or the prescription of the consumer patient; and
    a computer system communicatively coupled to the tracking device and configured to:
        receive each unique IEM identifier code read from each interrogated IEM; and
        store each unique IEM identifier code with at least one of its respective pharmaceutical product co-encapsulated with the IEM or the prescription, into the database; and
a transmission unit configured to transmit each received unique IEM identifier code and the identifier of the pharmaceutical composition linked to each received unique IEM identifier code to an IEM tracking system database for use in tracking consumer patient adherence to at least one active drug and dose form.

* * * * *